(12) United States Patent
Kakimoto et al.

(10) Patent No.: US 7,741,049 B2
(45) Date of Patent: Jun. 22, 2010

(54) ANALYSIS OF AGONIST-ACTIVITY AND ANTAGONIST-ACTIVITY TO CYTOKININ RECEPTOR

(75) Inventors: Tatsuo Kakimoto, Toyonaka (JP); Masayuki Higuchi, Okayama (JP); Tsutomu Inoue, Osaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/918,508

(22) Filed: Aug. 1, 2001

(65) Prior Publication Data

US 2002/0177162 A1    Nov. 28, 2002

(30) Foreign Application Priority Data

Mar. 15, 2001    (JP)    ............................. 2001-073812

(51) Int. Cl.
*G01N 33/53*    (2006.01)
*C12N 5/02*    (2006.01)
*C12N 15/82*    (2006.01)

(52) U.S. Cl. ......................... 435/7.1; 435/410; 435/468

(58) Field of Classification Search ................. 436/503; 435/7.1, 69.1, 183, 255.1, 254.21; 530/350; 536/23.2

See application file for complete search history.

(56) References Cited

U.S. PATENT DOCUMENTS

| | | | |
|---|---|---|---|
| 5,194,596 A * | 3/1993 | Tischer et al. ............... | 530/399 |
| 5,350,836 A * | 9/1994 | Kopchick et al. ........... | 530/399 |
| 6,077,682 A | 6/2000 | Inouye et al. | |
| 6,245,970 B1 * | 6/2001 | Frommer .................... | 800/298 |
| 7,026,530 B2 * | 4/2006 | Benfey et al. ............... | 800/298 |
| 2002/0173017 A1 * | 11/2002 | Benfey et al. ............... | 435/183 |

FOREIGN PATENT DOCUMENTS

| | | |
|---|---|---|
| EP | 0 892 063 A2 | 1/1999 |
| EP | 1033405 A2 * | 9/2000 |
| WO | WO 99/36508 A1 | 7/1999 |
| WO | WO 02/099079 A2 * | 12/2002 |

OTHER PUBLICATIONS

Iwamura et al. (1983), Quantitative Aspects of the Receptor Binding of Cytokinin Agonists and Antagonists, J. Medicinal Chem., vol. 26, No. 6, pp. 838-844.*
Rashotte et al. (2003), Expression Profiling of Cytokinin Action in *Arabidopsis*, Plant Physiology, vol. 132, pp. 1998-2011.*
Estelle (1998), Cytokinin action: Two receptors better than one? Current Biology, vol. 8, pp. R539-R541.*
Schaller (1997), Ethylene and cytokinin signalling in plants: the role of two-component systems, Essays Biochem. vol. 32, pp. 101-111.*
Haberer et al. (2002), Cytokinins. New Insights into a Classic Phytohormone, Plant Physiology 128: 354-362.*
Iwamura et al., 1983, J Medicinal Chem. 26(6): 838-844 (copy provided with Office Action of Jan. 6, 2004).*
Bowie et al. Science. 1990. 247:1306-1310.*
Wells. Biochemistry 1990. 29:8509-8517.*
Holland et al., Biosystems. 1987; 20(2):181-206, Abstract Only.*
Skolnick et al. 2000, Trends in Biotech. 18:34-39.*
Bork. 2000, Genome Research 10:398-400.*
Doerks et al. 1998, Trends in Genetics 14:248-250.*
Smith et al. 1997, Nature Biotechnology 15:1222-1223.*
Brenner. 1999, Trends in Genetics 15:132-133.*
Bork et al. 1996, Trends in Genetics 12:425-427.*
Benjamin et al., 1998, Development 125:1591-1598.*
Vukicevic et al. 1996, PNAS USA 93:9021-9026.*
Massague. 1987, Cell 49:437-8.*
Pilbeam et al., 1993, Bone 14:717-720.*
T. Kakimoto, "Cytokinin signaling", Current Opinion in Plant Biology, Quadrant Subscription Services, GB, vol. 5, No. 1, 1998, pp. 399-403 (Abstract XP-001079011).
M. Estelle, "Cytokinin action: Two receptors better than one?", Current Biology, Current Science, GB, vol. 16, No. 8, 1998, pp. R539-R541 (Abstract XP-001071265).
Kulaeva et al., "A new family of cytokinin receptors from Cereales", FEBS Letters, vol. 423, No. 2, Feb. 20, 1998, pp. 239-242 (Abstract XP-002212288).
T. Inoue et al., "Identification of CRE1 as a cytokinin receptor from *Arabidopsis*", Nature, vol. 409, No. 6823, (Feb. 22, 2001), pp. 1060-1063 with Abstract XP-002199637.
A. P. Mahonen et al., "A novel two-component hybrid molecule regulates vascular morphogenesis of the *Arabidopsis* root", Genes & Development, vol. 14, No. 23, (Dec. 1, 2001), pp. 2938-2943.
T. Kakimoto, "CKI1, a Histidine Kinase Homolog Implicated in Cytokinin Signal Transduction", Science, American Association for the Advancement of Science, vol. 274, (Nov. 8, 1996), pp. 982-985.
Kakimoto et al., "2SF4 Roles of histidine kinases in cytokinin signal transduction", *Biophysics The biophysical Society of Japan*, vol. 40, Supplement 1, Aug. 5, 2000, p. S111, with English translation and accompanying Declaration.

(Continued)

*Primary Examiner*—Cherie M Woodward
(74) *Attorney, Agent, or Firm*—Sughrue Mion, PLLC

(57) ABSTRACT

The present invention provides a method for analyzing agonist-activity to a cytokinin receptor, which comprises (1) bringing an examinee substance into contact with a transformed cell into which DNA coding the cytokinin receptor is introduced and
(2) measuring the existence or the quantity of intracellular signal transduction from the cytokinin receptor expressed in the transformed cell, and, a method for analyzing antagonist-activity to a cytokinin receptor, which comprises (1) bringing an examinee substance and a substance having agonist-activity to the cytokinin receptor into contact with a transformed cell into which DNA coding the cytokinin receptor is introduced and
(2) measuring the existence or the quantity of intracellular signal transduction from the cytokinin receptor expressed in the transformed cell, and the like.

9 Claims, No Drawings

OTHER PUBLICATIONS

Inoue et al., "W1D3 A study on cytokinin signal transduction", *Program Workshop Abstracts of the 23rd Annual Meeting of The Molecular Biology Society of Japan*, Dec. 2000, p. 259, with English translation and accompanying Declaration.

Machida et al., "W1D-6 Plant cell growth controlled by the MAP kinase cascade mediated by NPK1 MAPKKK", *Program Workshop Abstracts of the 23rd Annual Meeting of The Molecular Biology Society of Japan*, Dec. 2000, p. 259, with English translation and accompanying Declaration.

Inoue et al., "4PC-312 Mutation in the histidine kinase gene T23K3.2 causes cytokinin-insensitive phenotype", *Program Workshop Abstracts of the 23rd Annual Meeting of The Molecular Biology Society of Japan*, Dec. 2000, p. 816, with English translation and accompanying Declaration.

Huguchi et al., "4PC-313 The product of the causal gene T23K3.2 for the cytokinin insensitive mutant functions as a cytokinin receptor in yeast," *Program Workshop Abstracts of the 23rd Annual Meeting of The Molecular Biology Society of Japan*, Dec. 2000, p. 817, with English translation and accompanying Declaration.

Kakimoto et al., "Success In Isolating A Receptor Of Cytokinin Which Increases Plant Growth, Onto Developing Agrochemicals", *Nikkei Biotech*, Mar. 12, 2001, p. 12, with English translation and accompanying Declaration.

Inoue et al., "Identification of CRE1 as a cytokinin receptor from *Arabidopsis*," *Nature*, vol. 409, Feb. 22, 2001, pp. 1060-1063.

Ueguchi et al., "Novel Family of Sensor Histidine Kinase Genes in *Arabidopsis thaliana*", *Plant Cell Physiol.*, vol. 42, No. 2, 2001, pp. 231-125.

Suzuki et al., "The *Arabidopsis* Sensor His-kinase, AHK4, Can Respond to Cytokinins", *Plant Cell Physiol.*, vol. 42, No. 2, 2001, pp. 107-113.

Maeda et al., "A two-component system that regulates an osmosensing MAP kinase cascade in yeast", *Nature*, vol. 369, May 19, 1994, pp. 242-245.

Urao et al., "A Transmembrane Hybrid-Type Histidine Kinase in *Arabidopsis* Functions as an Osmosensor", *The Plant Cell*, vol. 11, Sep. 1999, pp. 1743-1754.

* cited by examiner

```
                        SEQUENCE LISTING

<160> NUMBER OF SEQ ID NOS: 22

<210> SEQ ID NO 1
<211> LENGTH: 3531
<212> TYPE: DNA
<213> ORGANISM: Arabidopsis thaliana
<220> FEATURE:
<221> NAME/KEY: CDS
<222> LOCATION: (1)..(3531)

<400> SEQUENCE: 1 atg tct ata act tgt gag ctc ttg aat ctt act tca aag aaa gct aag      48
Met Ser Ile Thr Cys Glu Leu Leu Asn Leu Thr Ser Lys Lys Ala Lys
 1               5                  10                  15
```

|  |  |
|---|---|
| aag tcg tcg agc agt gac aag aaa tgg cta aag aag cct ctc ttc ttc<br>Lys Ser Ser Ser Ser Asp Lys Lys Trp Leu Lys Lys Pro Leu Phe Phe<br>20             25              30 | 96 |
| ctg att ttg tgt ggc tct ttg gta att gtt ttg gtt atg ttc tta cgg<br>Leu Ile Leu Cys Gly Ser Leu Val Ile Val Leu Val Met Phe Leu Arg<br>35              40              45 | 144 |
| tta ggt aga agt cag aag gag gag aca gat tct tgt aat gga gaa gag<br>Leu Gly Arg Ser Gln Lys Glu Glu Thr Asp Ser Cys Asn Gly Glu Glu<br>50              55              60 | 192 |
| aaa gtg ttg tat aga cat caa aat gtc aca aga agt gag att cat gat<br>Lys Val Leu Tyr Arg His Gln Asn Val Thr Arg Ser Glu Ile His Asp<br>65              70              75              80 | 240 |
| ttg gtc tct ttg ttc tct gat tca gat cag gta aca tcc ttt gaa tgt<br>Leu Val Ser Leu Phe Ser Asp Ser Asp Gln Val Thr Ser Phe Glu Cys<br>85              90              95 | 288 |
| cat aag gaa tca agc cct gga atg tgg aca aac tat ggt att aca tgt<br>His Lys Glu Ser Ser Pro Gly Met Trp Thr Asn Tyr Gly Ile Thr Cys<br>100             105             110 | 336 |
| tcc ctg agt gtg cgt tct gat aaa caa gag act aga ggg ctt ccc tgg<br>Ser Leu Ser Val Arg Ser Asp Lys Gln Glu Thr Arg Gly Leu Pro Trp<br>115             120             125 | 384 |
| aat ctt ggc tta gga cat tct atc tca tca aca tct tgt atg tgt ggt<br>Asn Leu Gly Leu Gly His Ser Ile Ser Ser Thr Ser Cys Met Cys Gly<br>130             135             140 | 432 |
| aat ctt gaa ccg att tta cag caa cct gaa aac ctt gag gaa gaa aac<br>Asn Leu Glu Pro Ile Leu Gln Gln Pro Glu Asn Leu Glu Glu Glu Asn<br>145             150             155             160 | 480 |
| cat gaa gaa ggg ctg gag cag ggt ttg tca tcg tat tta aga aat gca<br>His Glu Glu Gly Leu Glu Gln Gly Leu Ser Ser Tyr Leu Arg Asn Ala<br>165             170             175 | 528 |
| tgg tgg tgt cta atc ctt ggt gtg tta gtg tgc cat aag att tat gta<br>Trp Trp Cys Leu Ile Leu Gly Val Leu Val Cys His Lys Ile Tyr Val<br>180             185             190 | 576 |
| tct cat tct aaa gca cga ggt gag agg aaa gag aaa gta cat ctg caa<br>Ser His Ser Lys Ala Arg Gly Glu Arg Lys Glu Lys Val His Leu Gln<br>195             200             205 | 624 |
| gag gct tta gct cca aag aag cag caa caa cgt gct cag act tct tct<br>Glu Ala Leu Ala Pro Lys Lys Gln Gln Gln Arg Ala Gln Thr Ser Ser<br>210             215             220 | 672 |
| aga ggg gct gga aga tgg agg aag aat atc ctc ctc ctt ggt att tta<br>Arg Gly Ala Gly Arg Trp Arg Lys Asn Ile Leu Leu Leu Gly Ile Leu<br>225             230             235             240 | 720 |
| gga gga gtt tcc ttc tct gtt tgg tgg ttt tgg gac act aat gag gag<br>Gly Gly Val Ser Phe Ser Val Trp Trp Phe Trp Asp Thr Asn Glu Glu<br>245             250             255 | 768 |
| atc ata atg aaa agg agg gag act ttg gca aac atg tgt gac gaa cga<br>Ile Ile Met Lys Arg Arg Glu Thr Leu Ala Asn Met Cys Asp Glu Arg<br>260             265             270 | 816 |
| gca cgt gtt tta caa gat cag ttc aat gtt agc ttg aac cat gtt cat<br>Ala Arg Val Leu Gln Asp Gln Phe Asn Val Ser Leu Asn His Val His<br>275             280             285 | 864 |
| gcc ttg tct att ctt gta tct aca ttt cat cat ggt aaa atc cca tct<br>Ala Leu Ser Ile Leu Val Ser Thr Phe His His Gly Lys Ile Pro Ser<br>290             295             300 | 912 |
| gcc att gat cag aga aca ttt gaa gaa tat act gag aga aca aac ttt<br>Ala Ile Asp Gln Arg Thr Phe Glu Glu Tyr Thr Glu Arg Thr Asn Phe<br>305             310             315             320 | 960 |
| gag agg cca ctt act agt ggt gta gcg tat gct ttg aaa gtc cca cac<br>Glu Arg Pro Leu Thr Ser Gly Val Ala Tyr Ala Leu Lys Val Pro His<br>325             330             335 | 1008 |

| | | | | | | | | | | | | | | | | |
|---|---|---|---|---|---|---|---|---|---|---|---|---|---|---|---|---|
| tca | gaa | aga | gag | aaa | ttt | gaa | aag | gag | cat | gga | tgg | gca | ata | aag | aaa | 1056 |
| Ser | Glu | Arg | Glu | Lys | Phe | Glu | Lys | Glu | His | Gly | Trp | Ala | Ile | Lys | Lys | |
| | | 340 | | | | | 345 | | | | | 350 | | | | |
| atg | gaa | act | gag | gac | cag | aca | gtt | gta | caa | gat | tgt | gtt | cct | gaa | aac | 1104 |
| Met | Glu | Thr | Glu | Asp | Gln | Thr | Val | Val | Gln | Asp | Cys | Val | Pro | Glu | Asn | |
| | 355 | | | | | 360 | | | | | 365 | | | | | |
| ttt | gat | ccc | gca | ccg | att | caa | gac | gaa | tac | gcg | cca | gtt | ata | ttt | gct | 1152 |
| Phe | Asp | Pro | Ala | Pro | Ile | Gln | Asp | Glu | Tyr | Ala | Pro | Val | Ile | Phe | Ala | |
| 370 | | | | | 375 | | | | | 380 | | | | | | |
| caa | gaa | act | gtt | tcc | cat | att | gta | tcg | gtc | gac | atg | atg | tct | gga | gaa | 1200 |
| Gln | Glu | Thr | Val | Ser | His | Ile | Val | Ser | Val | Asp | Met | Met | Ser | Gly | Glu | |
| 385 | | | | | 390 | | | | | 395 | | | | | 400 | |
| gaa | gac | cgt | gaa | aac | atc | tta | cgg | gca | agg | gca | tca | gga | aaa | gga | gtg | 1248 |
| Glu | Asp | Arg | Glu | Asn | Ile | Leu | Arg | Ala | Arg | Ala | Ser | Gly | Lys | Gly | Val | |
| | | | | 405 | | | | | 410 | | | | | 415 | | |
| tta | aca | tct | cca | ttt | aag | ctt | ctt | aag | tca | aat | cat | ctt | ggt | gtt | gtg | 1296 |
| Leu | Thr | Ser | Pro | Phe | Lys | Leu | Leu | Lys | Ser | Asn | His | Leu | Gly | Val | Val | |
| | | | 420 | | | | | 425 | | | | | 430 | | | |
| ttg | acc | ttt | gct | gtc | tat | gac | acg | agc | cta | ccg | cct | gat | gct | aca | gaa | 1344 |
| Leu | Thr | Phe | Ala | Val | Tyr | Asp | Thr | Ser | Leu | Pro | Pro | Asp | Ala | Thr | Glu | |
| | | 435 | | | | | 440 | | | | | 445 | | | | |
| gaa | cag | cgt | gtt | gaa | gca | act | att | ggg | tac | ctt | ggt | gca | tca | tat | gat | 1392 |
| Glu | Gln | Arg | Val | Glu | Ala | Thr | Ile | Gly | Tyr | Leu | Gly | Ala | Ser | Tyr | Asp | |
| | 450 | | | | | 455 | | | | | 460 | | | | | |
| atg | cca | tcg | ctg | gtg | gag | aaa | ctt | ctt | cac | caa | ctt | gcc | agc | aaa | cag | 1440 |
| Met | Pro | Ser | Leu | Val | Glu | Lys | Leu | Leu | His | Gln | Leu | Ala | Ser | Lys | Gln | |
| 465 | | | | | 470 | | | | | 475 | | | | | 480 | |
| aca | att | gct | gtg | gat | gtt | tac | gac | aca | act | aac | act | tca | ggt | cta | ata | 1488 |
| Thr | Ile | Ala | Val | Asp | Val | Tyr | Asp | Thr | Thr | Asn | Thr | Ser | Gly | Leu | Ile | |
| | | | | 485 | | | | | 490 | | | | | 495 | | |
| aaa | atg | tat | ggc | tca | gaa | att | ggg | gat | ata | agt | gag | cag | cat | ata | agt | 1536 |
| Lys | Met | Tyr | Gly | Ser | Glu | Ile | Gly | Asp | Ile | Ser | Glu | Gln | His | Ile | Ser | |
| | | | 500 | | | | | 505 | | | | | 510 | | | |
| agc | ctt | gat | ttt | ggt | gat | cca | tca | agg | aac | cat | gag | atg | cat | tgc | agg | 1584 |
| Ser | Leu | Asp | Phe | Gly | Asp | Pro | Ser | Arg | Asn | His | Glu | Met | His | Cys | Arg | |
| | | 515 | | | | | 520 | | | | | 525 | | | | |
| ttt | aag | cat | aaa | ctt | ccc | att | ccc | tgg | aca | gcg | ata | aca | ccg | tcg | atc | 1632 |
| Phe | Lys | His | Lys | Leu | Pro | Ile | Pro | Trp | Thr | Ala | Ile | Thr | Pro | Ser | Ile | |
| | 530 | | | | | 535 | | | | | 540 | | | | | |
| tta | gtt | ctg | gtt | att | act | ttt | ctt | gtt | ggt | tat | att | tta | tat | gaa | gcc | 1680 |
| Leu | Val | Leu | Val | Ile | Thr | Phe | Leu | Val | Gly | Tyr | Ile | Leu | Tyr | Glu | Ala | |
| 545 | | | | | 550 | | | | | 555 | | | | | 560 | |
| atc | aac | cga | att | gcg | aca | gtt | gaa | gag | gat | tgt | cag | aag | atg | agg | gaa | 1728 |
| Ile | Asn | Arg | Ile | Ala | Thr | Val | Glu | Glu | Asp | Cys | Gln | Lys | Met | Arg | Glu | |
| | | | | 565 | | | | | 570 | | | | | 575 | | |
| ctc | aaa | gct | cgt | gct | gag | gcc | gct | gac | att | gca | aag | tca | cag | ttc | cta | 1776 |
| Leu | Lys | Ala | Arg | Ala | Glu | Ala | Ala | Asp | Ile | Ala | Lys | Ser | Gln | Phe | Leu | |
| | | | 580 | | | | | 585 | | | | | 590 | | | |
| gca | act | gtt | tct | cat | gag | ata | cgg | act | ccg | atg | aat | gga | gtt | tta | gga | 1824 |
| Ala | Thr | Val | Ser | His | Glu | Ile | Arg | Thr | Pro | Met | Asn | Gly | Val | Leu | Gly | |
| | | 595 | | | | | 600 | | | | | 605 | | | | |
| atg | ctg | aaa | atg | ctg | atg | gac | acc | gat | ctt | gat | gcg | aag | cag | atg | gac | 1872 |
| Met | Leu | Lys | Met | Leu | Met | Asp | Thr | Asp | Leu | Asp | Ala | Lys | Gln | Met | Asp | |
| | 610 | | | | | 615 | | | | | 620 | | | | | |
| tat | gcg | caa | act | gct | cat | ggc | agt | ggg | aag | gat | ctt | aca | tca | cta | ata | 1920 |
| Tyr | Ala | Gln | Thr | Ala | His | Gly | Ser | Gly | Lys | Asp | Leu | Thr | Ser | Leu | Ile | |
| 625 | | | | | 630 | | | | | 635 | | | | | 640 | |
| aat | gag | gtt | ctt | gat | cag | gca | aag | att | gaa | tcc | gga | agg | ctc | gag | ctt | 1968 |
| Asn | Glu | Val | Leu | Asp | Gln | Ala | Lys | Ile | Glu | Ser | Gly | Arg | Leu | Glu | Leu | |

-continued

```
                       645                 650                 655
gaa aat gtg cct ttt gat atg cgt ttt att ctt gat aat gtt tca tct    2016
Glu Asn Val Pro Phe Asp Met Arg Phe Ile Leu Asp Asn Val Ser Ser
            660                 665                 670 ctc ctc tct ggc aag gca aat gaa aaa gga att gag ttg gcc gtt tat    2064
Leu Leu Ser Gly Lys Ala Asn Glu Lys Gly Ile Glu Leu Ala Val Tyr
675                 680                 685 gtt tct agt caa gtt cct gat gtt gta gtc ggt gat ccg agt cgg ttc    2112
Val Ser Ser Gln Val Pro Asp Val Val Val Gly Asp Pro Ser Arg Phe
    690                 695                 700 cgg cag atc att aca aac ctg gtt gga aac tca atc aaa ttc aca cag    2160
Arg Gln Ile Ile Thr Asn Leu Val Gly Asn Ser Ile Lys Phe Thr Gln
705                 710                 715                 720 gaa agg gga cac ata ttt atc tca gtg cac ctt gca gat gag gta aag    2208
Glu Arg Gly His Ile Phe Ile Ser Val His Leu Ala Asp Glu Val Lys
                725                 730                 735 gag cct ctt act att gaa gac gca gtg cta aaa cag cga cta gct tta    2256
Glu Pro Leu Thr Ile Glu Asp Ala Val Leu Lys Gln Arg Leu Ala Leu
            740                 745                 750 gga tgc agc gag tcc ggt gag aca gtt agc ggg ttt cct gcg gta aat    2304
Gly Cys Ser Glu Ser Gly Glu Thr Val Ser Gly Phe Pro Ala Val Asn
        755                 760                 765 gca tgg gga agc tgg aag aat ttc aag aca tgt tac agt act gag agt    2352
Ala Trp Gly Ser Trp Lys Asn Phe Lys Thr Cys Tyr Ser Thr Glu Ser
770                 775                 780 cag aat tct gat caa atc aaa ttg cta gtt aca gtg gag gac act gga    2400
Gln Asn Ser Asp Gln Ile Lys Leu Leu Val Thr Val Glu Asp Thr Gly
785                 790                 795                 800 gtt ggc ata cct gtg gat gca caa ggc cga atc ttc aca cct ttt atg    2448
Val Gly Ile Pro Val Asp Ala Gln Gly Arg Ile Phe Thr Pro Phe Met
                805                 810                 815 caa gcc gac agt tcc aca tcg cgg act tat ggt gga act ggc ata ggt    2496
Gln Ala Asp Ser Ser Thr Ser Arg Thr Tyr Gly Gly Thr Gly Ile Gly
            820                 825                 830 ttg agt ata agc aaa cgt ttg gtt gaa ctc atg caa gga gag atg ggg    2544
Leu Ser Ile Ser Lys Arg Leu Val Glu Leu Met Gln Gly Glu Met Gly
        835                 840                 845 ttt gtg agt gag ccc ggg ata ggc agt act ttt tca ttt act gga gtt    2592
Phe Val Ser Glu Pro Gly Ile Gly Ser Thr Phe Ser Phe Thr Gly Val
850                 855                 860 ttc ggg aaa gca gaa aca aat acg tcg att act aag ctg gaa cga ttc    2640
Phe Gly Lys Ala Glu Thr Asn Thr Ser Ile Thr Lys Leu Glu Arg Phe
865                 870                 875                 880 gat cta gct att cag gag ttt aca gga ttg aga gca tta gtt att gat    2688
Asp Leu Ala Ile Gln Glu Phe Thr Gly Leu Arg Ala Leu Val Ile Asp
                885                 890                 895 aac aga aac att aga gca gag gtc acc agg tac gaa ctt cgg aga ctg    2736
Asn Arg Asn Ile Arg Ala Glu Val Thr Arg Tyr Glu Leu Arg Arg Leu
            900                 905                 910 gga ata tct gca gac att gtt tca agt ctg aga atg gca tgc act tgt    2784
Gly Ile Ser Ala Asp Ile Val Ser Ser Leu Arg Met Ala Cys Thr Cys
        915                 920                 925 tgt atc agc aaa tta gaa aat ttg gct atg att cta ata gac aaa gac    2832
Cys Ile Ser Lys Leu Glu Asn Leu Ala Met Ile Leu Ile Asp Lys Asp
930                 935                 940 gcc tgg aac aag gaa gaa ttt tca gta ctt gac gag ttg ttt acc cga    2880
Ala Trp Asn Lys Glu Glu Phe Ser Val Leu Asp Glu Leu Phe Thr Arg
945                 950                 955                 960 agc aaa gta acc ttt aca aga gtc cca aag att ttt ctt ttg gca act    2928
Ser Lys Val Thr Phe Thr Arg Val Pro Lys Ile Phe Leu Leu Ala Thr
```

-continued

```
Ser Lys Val Thr Phe Thr Arg Val Pro Lys Ile Phe Leu Leu Ala Thr
            965                 970                 975 tct gca act ctt act gag cgc agt gag atg aag tct act ggt ctc atc         2976
Ser Ala Thr Leu Thr Glu Arg Ser Glu Met Lys Ser Thr Gly Leu Ile
            980                 985                 990 gat gag gtg gtg ata aag cct ctt cgg atg agt gtc tta ata tgt tgc         3024
Asp Glu Val Val Ile Lys Pro Leu Arg Met Ser Val Leu Ile Cys Cys
            995                 1000                1005 ttg caa gaa acc ctt gtc aat ggc aag aag agg caa ccg aac aga cag         3072
Leu Gln Glu Thr Leu Val Asn Gly Lys Lys Arg Gln Pro Asn Arg Gln
    1010                1015                1020 cga aga aat ctt gga cac ttg cta aga gaa aaa cag att ctg gtt gtg         3120
Arg Arg Asn Leu Gly His Leu Leu Arg Glu Lys Gln Ile Leu Val Val
1025                1030                1035                1040 gat gat aat ctt gtg aac aga cga gtt gca gaa ggt gca ctt aag aaa         3168
Asp Asp Asn Leu Val Asn Arg Arg Val Ala Glu Gly Ala Leu Lys Lys
            1045                1050                1055 tat gga gct att gtt aca tgc gtt gag agt ggc aaa gct gca ttg gca         3216
Tyr Gly Ala Ile Val Thr Cys Val Glu Ser Gly Lys Ala Ala Leu Ala
            1060                1065                1070 atg ctt aag ccg cct cat aac ttc gat gct tgc ttc atg gat ctc cag         3264
Met Leu Lys Pro Pro His Asn Phe Asp Ala Cys Phe Met Asp Leu Gln
            1075                1080                1085 atg cct gaa atg gat gga ttt gaa gca aca agg aga gtc cgt gag ctg         3312
Met Pro Glu Met Asp Gly Phe Glu Ala Thr Arg Arg Val Arg Glu Leu
    1090                1095                1100 gag agg gaa atc aat aag aaa ata gct tct gga gaa gtt tca gct gaa         3360
Glu Arg Glu Ile Asn Lys Lys Ile Ala Ser Gly Glu Val Ser Ala Glu
1105                1110                1115                1120 atg ttc tgt aaa ttt agt agt tgg cac gtc ccg ata tta gca atg aca         3408
Met Phe Cys Lys Phe Ser Ser Trp His Val Pro Ile Leu Ala Met Thr
            1125                1130                1135 gca gat gtt att cag gct act cat gaa gaa tgc atg aaa tgt gga atg         3456
Ala Asp Val Ile Gln Ala Thr His Glu Glu Cys Met Lys Cys Gly Met
            1140                1145                1150 gat ggt tat gta tca aaa ccg ttt gaa gag gaa gtg ctc tac aca gcg         3504
Asp Gly Tyr Val Ser Lys Pro Phe Glu Glu Glu Val Leu Tyr Thr Ala
            1155                1160                1165 gta gca aga ttc ttt gaa cct tgt taa                                     3531
Val Ala Arg Phe Phe Glu Pro Cys
    1170                1175

<210> SEQ ID NO 2
<211> LENGTH: 1176
<212> TYPE: PRT
<213> ORGANISM: Arabidopsis thaliana

<400> SEQUENCE: 2

Met Ser Ile Thr Cys Glu Leu Leu Asn Leu Thr Ser Lys Lys Ala Lys
1               5                   10                  15

Lys Ser Ser Ser Ser Asp Lys Lys Trp Leu Lys Lys Pro Leu Phe Phe
            20                  25                  30

Leu Ile Leu Cys Gly Ser Leu Val Ile Val Leu Val Met Phe Leu Arg
        35                  40                  45

Leu Gly Arg Ser Gln Lys Glu Glu Thr Asp Ser Cys Asn Gly Glu Glu
    50                  55                  60

Lys Val Leu Tyr Arg His Gln Asn Val Thr Arg Ser Glu Ile His Asp
65                  70                  75                  80

Leu Val Ser Leu Phe Ser Asp Ser Asp Gln Val Thr Ser Phe Glu Cys
```

-continued

```
                85                  90                  95
His Lys Glu Ser Ser Pro Gly Met Trp Thr Asn Tyr Gly Ile Thr Cys
                100                 105                 110

Ser Leu Ser Val Arg Ser Asp Lys Gln Glu Thr Arg Gly Leu Pro Trp
            115                 120                 125

Asn Leu Gly Leu Gly His Ser Ile Ser Ser Thr Ser Cys Met Cys Gly
        130                 135                 140

Asn Leu Glu Pro Ile Leu Gln Gln Pro Glu Asn Leu Glu Glu Glu Asn
145                 150                 155                 160

His Glu Glu Gly Leu Glu Gln Gly Leu Ser Ser Tyr Leu Arg Asn Ala
                165                 170                 175

Trp Trp Cys Leu Ile Leu Gly Val Leu Val Cys His Lys Ile Tyr Val
                180                 185                 190

Ser His Ser Lys Ala Arg Gly Glu Arg Lys Glu Lys Val His Leu Gln
            195                 200                 205

Glu Ala Leu Ala Pro Lys Lys Gln Gln Gln Arg Ala Gln Thr Ser Ser
        210                 215                 220

Arg Gly Ala Gly Arg Trp Arg Lys Asn Ile Leu Leu Leu Gly Ile Leu
225                 230                 235                 240

Gly Gly Val Ser Phe Ser Val Trp Trp Phe Trp Asp Thr Asn Glu Glu
                245                 250                 255

Ile Ile Met Lys Arg Arg Glu Thr Leu Ala Asn Met Cys Asp Glu Arg
                260                 265                 270

Ala Arg Val Leu Gln Asp Gln Phe Asn Val Ser Leu Asn His Val His
            275                 280                 285

Ala Leu Ser Ile Leu Val Ser Thr Phe His His Gly Lys Ile Pro Ser
        290                 295                 300

Ala Ile Asp Gln Arg Thr Phe Glu Glu Tyr Thr Glu Arg Thr Asn Phe
305                 310                 315                 320

Glu Arg Pro Leu Thr Ser Gly Val Ala Tyr Ala Leu Lys Val Pro His
                325                 330                 335

Ser Glu Arg Glu Lys Phe Glu Lys Glu His Gly Trp Ala Ile Lys Lys
                340                 345                 350

Met Glu Thr Glu Asp Gln Thr Val Val Gln Asp Cys Val Pro Glu Asn
            355                 360                 365

Phe Asp Pro Ala Pro Ile Gln Asp Glu Tyr Ala Pro Val Ile Phe Ala
        370                 375                 380

Gln Glu Thr Val Ser His Ile Val Ser Val Asp Met Met Ser Gly Glu
385                 390                 395                 400

Glu Asp Arg Glu Asn Ile Leu Arg Ala Arg Ala Ser Gly Lys Gly Val
                405                 410                 415

Leu Thr Ser Pro Phe Lys Leu Leu Lys Ser Asn His Leu Gly Val Val
                420                 425                 430

Leu Thr Phe Ala Val Tyr Asp Thr Ser Leu Pro Pro Asp Ala Thr Glu
            435                 440                 445

Glu Gln Arg Val Glu Ala Thr Ile Gly Tyr Leu Gly Ala Ser Tyr Asp
        450                 455                 460

Met Pro Ser Leu Val Glu Lys Leu Leu His Gln Leu Ala Ser Lys Gln
465                 470                 475                 480

Thr Ile Ala Val Asp Val Tyr Asp Thr Thr Asn Thr Ser Gly Leu Ile
                485                 490                 495

Lys Met Tyr Gly Ser Glu Ile Gly Asp Ile Ser Glu Gln His Ile Ser
                500                 505                 510
```

```
Ser Leu Asp Phe Gly Asp Pro Ser Arg Asn His Glu Met His Cys Arg
            515                 520                 525

Phe Lys His Lys Leu Pro Ile Pro Trp Thr Ala Ile Thr Pro Ser Ile
        530                 535                 540

Leu Val Leu Val Ile Thr Phe Leu Val Gly Tyr Ile Leu Tyr Glu Ala
545                 550                 555                 560

Ile Asn Arg Ile Ala Thr Val Glu Glu Asp Cys Gln Lys Met Arg Glu
                565                 570                 575

Leu Lys Ala Arg Ala Glu Ala Asp Ile Ala Lys Ser Gln Phe Leu
            580                 585                 590

Ala Thr Val Ser His Glu Ile Arg Thr Pro Met Asn Gly Val Leu Gly
        595                 600                 605

Met Leu Lys Met Leu Met Asp Thr Asp Leu Asp Ala Lys Gln Met Asp
    610                 615                 620

Tyr Ala Gln Thr Ala His Gly Ser Gly Lys Asp Leu Thr Ser Leu Ile
625                 630                 635                 640

Asn Glu Val Leu Asp Gln Ala Lys Ile Glu Ser Gly Arg Leu Glu Leu
                645                 650                 655

Glu Asn Val Pro Phe Asp Met Arg Phe Ile Leu Asp Asn Val Ser Ser
            660                 665                 670

Leu Leu Ser Gly Lys Ala Asn Glu Lys Gly Ile Glu Leu Ala Val Tyr
        675                 680                 685

Val Ser Ser Gln Val Pro Asp Val Val Gly Asp Pro Ser Arg Phe
    690                 695                 700

Arg Gln Ile Ile Thr Asn Leu Val Gly Asn Ser Ile Lys Phe Thr Gln
705                 710                 715                 720

Glu Arg Gly His Ile Phe Ile Ser Val His Leu Ala Asp Glu Val Lys
                725                 730                 735

Glu Pro Leu Thr Ile Glu Asp Ala Val Leu Lys Gln Arg Leu Ala Leu
            740                 745                 750

Gly Cys Ser Glu Ser Gly Glu Thr Val Ser Gly Phe Pro Ala Val Asn
        755                 760                 765

Ala Trp Gly Ser Trp Lys Asn Phe Lys Thr Cys Tyr Ser Thr Glu Ser
    770                 775                 780

Gln Asn Ser Asp Gln Ile Lys Leu Leu Val Thr Val Glu Asp Thr Gly
785                 790                 795                 800

Val Gly Ile Pro Val Asp Ala Gln Gly Arg Ile Phe Thr Pro Phe Met
                805                 810                 815

Gln Ala Asp Ser Ser Thr Ser Arg Thr Tyr Gly Gly Thr Gly Ile Gly
            820                 825                 830

Leu Ser Ile Ser Lys Arg Leu Val Glu Leu Met Gln Gly Glu Met Gly
        835                 840                 845

Phe Val Ser Glu Pro Gly Ile Gly Ser Thr Ser Phe Thr Gly Val
    850                 855                 860

Phe Gly Lys Ala Glu Thr Asn Thr Ser Ile Thr Lys Leu Glu Arg Phe
865                 870                 875                 880

Asp Leu Ala Ile Gln Glu Phe Thr Gly Leu Arg Ala Leu Val Ile Asp
                885                 890                 895

Asn Arg Asn Ile Arg Ala Glu Val Thr Arg Tyr Glu Leu Arg Arg Leu
            900                 905                 910

Gly Ile Ser Ala Asp Ile Val Ser Ser Leu Arg Met Ala Cys Thr Cys
        915                 920                 925
```

```
Cys Ile Ser Lys Leu Glu Asn Leu Ala Met Ile Leu Ile Asp Lys Asp
    930                 935                 940

Ala Trp Asn Lys Glu Glu Phe Ser Val Leu Asp Glu Leu Phe Thr Arg
945                 950                 955                 960

Ser Lys Val Thr Phe Thr Arg Val Pro Lys Ile Phe Leu Leu Ala Thr
                965                 970                 975

Ser Ala Thr Leu Thr Glu Arg Ser Glu Met Lys Ser Thr Gly Leu Ile
            980                 985                 990

Asp Glu Val Val Ile Lys Pro Leu Arg Met Ser Val Leu Ile Cys Cys
        995                 1000                1005

Leu Gln Glu Thr Leu Val Asn Gly Lys Lys Arg Gln Pro Asn Arg Gln
    1010                1015                1020

Arg Arg Asn Leu Gly His Leu Leu Arg Glu Lys Gln Ile Leu Val Val
1025                1030                1035                1040

Asp Asp Asn Leu Val Asn Arg Val Ala Glu Gly Ala Leu Lys Lys
                1045                1050                1055

Tyr Gly Ala Ile Val Thr Cys Val Glu Ser Gly Lys Ala Ala Leu Ala
            1060                1065                1070

Met Leu Lys Pro Pro His Asn Phe Asp Ala Cys Phe Met Asp Leu Gln
            1075                1080                1085

Met Pro Glu Met Asp Gly Phe Glu Ala Thr Arg Arg Val Arg Glu Leu
    1090                1095                1100

Glu Arg Glu Ile Asn Lys Lys Ile Ala Ser Gly Glu Val Ser Ala Glu
1105                1110                1115                1120

Met Phe Cys Lys Phe Ser Ser Trp His Val Pro Ile Leu Ala Met Thr
                1125                1130                1135

Ala Asp Val Ile Gln Ala Thr His Glu Glu Cys Met Lys Cys Gly Met
            1140                1145                1150

Asp Gly Tyr Val Ser Lys Pro Phe Glu Glu Glu Val Leu Tyr Thr Ala
            1155                1160                1165

Val Ala Arg Phe Phe Glu Pro Cys
    1170                1175

<210> SEQ ID NO 3
<211> LENGTH: 3111
<212> TYPE: DNA
<213> ORGANISM: Arabidopsis thaliana
<220> FEATURE:
<221> NAME/KEY: CDS
<222> LOCATION: (1)..(3111)

<400> SEQUENCE: 3 atg agt ctg ttc cat gtg cta ggg ttt ggt gtc aag att ggg cat ctc      48
Met Ser Leu Phe His Val Leu Gly Phe Gly Val Lys Ile Gly His Leu
 1               5                  10                  15 ttc tgg atg cta tgc tgc tgg ttt gtt tct tgg ttc gtt gat aat ggg      96
Phe Trp Met Leu Cys Cys Trp Phe Val Ser Trp Phe Val Asp Asn Gly
             20                  25                  30 atc gag gac aag tct ggt ctt tta gtt ggc tct gtc ggt gat ctt gag     144
Ile Glu Asp Lys Ser Gly Leu Leu Val Gly Ser Val Gly Asp Leu Glu
         35                  40                  45 aag act aag atg act acg ttg aag aag aag aac aag atg tgg ttc tgg     192
Lys Thr Lys Met Thr Thr Leu Lys Lys Lys Asn Lys Met Trp Phe Trp
     50                  55                  60 aat aag atc tct agc agc gga ctc aag atc ccg agt ttc tct tat cag     240
Asn Lys Ile Ser Ser Ser Gly Leu Lys Ile Pro Ser Phe Ser Tyr Gln
 65                  70                  75                  80
```

| | | |
|---|---|---|
| ttt ctt ggc tct gtt aaa ttc aac aag gcg tgg tgg agg aag ctt gtg<br>Phe Leu Gly Ser Val Lys Phe Asn Lys Ala Trp Trp Arg Lys Leu Val<br>                  85                       90                    95 | 288 |
| gtg gtt tgg gtt gtc ttc tgg gtc ttg gtc tct att tgg acg ttt tgg<br>Val Val Trp Val Val Phe Trp Val Leu Val Ser Ile Trp Thr Phe Trp<br>         100                    105                    110 | 336 |
| tac ttt agc tcg caa gct atg gag aag agg aaa gag acg cta gct agt<br>Tyr Phe Ser Ser Gln Ala Met Glu Lys Arg Lys Glu Thr Leu Ala Ser<br>         115                    120                    125 | 384 |
| atg tgt gat gag aga gct cgt atg ctg cag gat cag ttc aac gtt agc<br>Met Cys Asp Glu Arg Ala Arg Met Leu Gln Asp Gln Phe Asn Val Ser<br>130                   135                    140 | 432 |
| atg aat cat gtt caa gcc atg tct atc ttg atc tca acc ttc cac cat<br>Met Asn His Val Gln Ala Met Ser Ile Leu Ile Ser Thr Phe His His<br>145                   150                   155                160 | 480 |
| ggc aag att cct tct gct atc gat cag aga aca ttc tca gag tac act<br>Gly Lys Ile Pro Ser Ala Ile Asp Gln Arg Thr Phe Ser Glu Tyr Thr<br>                  165                    170                  175 | 528 |
| gat aga act tcc ttt gag agg cct ctt act agc ggg gta gct tat gct<br>Asp Arg Thr Ser Phe Glu Arg Pro Leu Thr Ser Gly Val Ala Tyr Ala<br>         180                    185                    190 | 576 |
| atg agg gtg ctc cat tca gag agg gaa gag ttc gag agg caa caa ggt<br>Met Arg Val Leu His Ser Glu Arg Glu Glu Phe Glu Arg Gln Gln Gly<br>         195                    200                    205 | 624 |
| tgg act att agg aag atg tat tct ctt gaa caa aac cca gtt cac aag<br>Trp Thr Ile Arg Lys Met Tyr Ser Leu Glu Gln Asn Pro Val His Lys<br>         210                    215                    220 | 672 |
| gat gac tat gac ctg gaa gct ttg gaa cca tcc cct gtc caa gaa gag<br>Asp Asp Tyr Asp Leu Glu Ala Leu Glu Pro Ser Pro Val Gln Glu Glu<br>225                   230                    235                240 | 720 |
| tac gct cca gtc atc ttt gct cag gac act gtt tct cac gtt gtt tct<br>Tyr Ala Pro Val Ile Phe Ala Gln Asp Thr Val Ser His Val Val Ser<br>                  245                    250                  255 | 768 |
| ctc gat atg ctg tct ggg aaa gaa gat cgt gaa aac gtt ttg cgg gcc<br>Leu Asp Met Leu Ser Gly Lys Glu Asp Arg Glu Asn Val Leu Arg Ala<br>         260                    265                    270 | 816 |
| agg agt tca ggt aaa ggg gtt ttg aca gct cct ttc cca ttg ata aag<br>Arg Ser Ser Gly Lys Gly Val Leu Thr Ala Pro Phe Pro Leu Ile Lys<br>             275                    280                    285 | 864 |
| aca aat aga ctt ggg gtg atc ctg aca ttt gca gtg tac aag aga gat<br>Thr Asn Arg Leu Gly Val Ile Leu Thr Phe Ala Val Tyr Lys Arg Asp<br>         290                    295                    300 | 912 |
| ctc ccc tcc aat gca acg cca aaa gag aga att gag gct act aac ggg<br>Leu Pro Ser Asn Ala Thr Pro Lys Glu Arg Ile Glu Ala Thr Asn Gly<br>305                   310                    315                320 | 960 |
| tat ctc ggg gga gtg ttt gac att gag tcc ctg gta gaa aac ttg ctt<br>Tyr Leu Gly Gly Val Phe Asp Ile Glu Ser Leu Val Glu Asn Leu Leu<br>                  325                    330                  335 | 1008 |
| caa cag ctg gct agc aag caa acg att ctt gtc aat gtg tac gat atc<br>Gln Gln Leu Ala Ser Lys Gln Thr Ile Leu Val Asn Val Tyr Asp Ile<br>         340                    345                    350 | 1056 |
| acc aat cac tct caa ccg att agc atg tat ggt aca aat gtg tcg gct<br>Thr Asn His Ser Gln Pro Ile Ser Met Tyr Gly Thr Asn Val Ser Ala<br>             355                    360                    365 | 1104 |
| gat ggg ttg gaa cgt gtt agt cca cta atc ttt ggc gat cca ttg aga<br>Asp Gly Leu Glu Arg Val Ser Pro Leu Ile Phe Gly Asp Pro Leu Arg<br>         370                    375                    380 | 1152 |
| aag cat gag atg cgt tgc aga ttt aag cag aaa cca cca tgg cca gtg<br>Lys His Glu Met Arg Cys Arg Phe Lys Gln Lys Pro Pro Trp Pro Val<br>385                   390                    395                400 | 1200 |

```
cta tca atg gtg aca tca ttc ggt atc ctt gtg att gcg tta ctt gtt   1248
Leu Ser Met Val Thr Ser Phe Gly Ile Leu Val Ile Ala Leu Leu Val
            405                 410                 415 gca cat ata atc cac gca acc gtt agt cga ata cac aaa gtt gaa gaa   1296
Ala His Ile Ile His Ala Thr Val Ser Arg Ile His Lys Val Glu Glu
            420                 425                 430 gat tgt gat aaa atg aag cag ctc aag aaa aag gct gaa gca gca gat   1344
Asp Cys Asp Lys Met Lys Gln Leu Lys Lys Lys Ala Glu Ala Ala Asp
            435                 440                 445 gtt gca aag tca cag ttc ctt gcc act gtt tca cat gaa atc aga act   1392
Val Ala Lys Ser Gln Phe Leu Ala Thr Val Ser His Glu Ile Arg Thr
450                 455                 460 cca atg aat ggt gtt cta gga atg ttg cat atg ctt atg gac aca gag   1440
Pro Met Asn Gly Val Leu Gly Met Leu His Met Leu Met Asp Thr Glu
465                 470                 475                 480 tta gat gtt acg caa cag gat tat gtt agg acc gca cag gca agt gga   1488
Leu Asp Val Thr Gln Gln Asp Tyr Val Arg Thr Ala Gln Ala Ser Gly
            485                 490                 495 aaa gct tta gtc tcg cta ata aat gag gtt ttg gac caa gca aag att   1536
Lys Ala Leu Val Ser Leu Ile Asn Glu Val Leu Asp Gln Ala Lys Ile
            500                 505                 510 gaa tct gga aag ctt gaa ctt gag gag gtg cgg ttt gat ttg aga gga   1584
Glu Ser Gly Lys Leu Glu Leu Glu Glu Val Arg Phe Asp Leu Arg Gly
            515                 520                 525 ata tta gat gat gtc ctg tca ctc ttc tct agc aag tcc caa caa aag   1632
Ile Leu Asp Asp Val Leu Ser Leu Phe Ser Ser Lys Ser Gln Gln Lys
530                 535                 540 ggg gtg gag ttg gca gta tac ata tct gat cgt gtt cca gat atg tta   1680
Gly Val Glu Leu Ala Val Tyr Ile Ser Asp Arg Val Pro Asp Met Leu
545                 550                 555                 560 att ggt gat cct ggg agg ttt cga caa ata ctc aca aat ctt atg ggt   1728
Ile Gly Asp Pro Gly Arg Phe Arg Gln Ile Leu Thr Asn Leu Met Gly
            565                 570                 575 aat tcc att aag ttc act gag aaa gga cac atc ttt gta act gtt cat   1776
Asn Ser Ile Lys Phe Thr Glu Lys Gly His Ile Phe Val Thr Val His
            580                 585                 590 ttg gtg gat gag cta ttt gaa tct atc gat gga gag aca gca tca tct   1824
Leu Val Asp Glu Leu Phe Glu Ser Ile Asp Gly Glu Thr Ala Ser Ser
            595                 600                 605 ccg gaa agt aca ctg agt ggg ctt cca gtt gca gac cgg cag agg agc   1872
Pro Glu Ser Thr Leu Ser Gly Leu Pro Val Ala Asp Arg Gln Arg Ser
610                 615                 620 tgg gaa aac ttt aaa gct ttc agc tcc aac ggg cat cgg agc ttt gaa   1920
Trp Glu Asn Phe Lys Ala Phe Ser Ser Asn Gly His Arg Ser Phe Glu
625                 630                 635                 640 cca tct ccc cct gat ata aac cta atc gtc tca gtt gag gat act ggc   1968
Pro Ser Pro Pro Asp Ile Asn Leu Ile Val Ser Val Glu Asp Thr Gly
            645                 650                 655 gta ggg atc cct gta gaa gcg cag tcc cgt att ttt acg cct ttc atg   2016
Val Gly Ile Pro Val Glu Ala Gln Ser Arg Ile Phe Thr Pro Phe Met
            660                 665                 670 caa gtc gga cca tcc ata tcc agg acg cat gga ggc aca gga att gga   2064
Gln Val Gly Pro Ser Ile Ser Arg Thr His Gly Gly Thr Gly Ile Gly
            675                 680                 685 ctt agc ata agc aaa tgt cta gtt gga ctg atg aag gga gaa att gga   2112
Leu Ser Ile Ser Lys Cys Leu Val Gly Leu Met Lys Gly Glu Ile Gly
            690                 695                 700 ttc tcg agt act ccc aag gtt ggg tcc aca ttc aca ttt act gct gta   2160
Phe Ser Ser Thr Pro Lys Val Gly Ser Thr Phe Thr Phe Thr Ala Val
```

-continued

| | | |
|---|---|---|
| ttt tcc aat ggg atg caa cca gct gaa aga aag aat gac aac aac cag<br>Phe Ser Asn Gly Met Gln Pro Ala Glu Arg Lys Asn Asp Asn Asn Gln<br>705                    710                    715                    720 | 2208 |
| ccc ata ttc tcg gaa ttc cgg ggc atg aaa gct gtg gtt gtg gac cat<br>Pro Ile Phe Ser Glu Phe Arg Gly Met Lys Ala Val Val Val Asp His<br>         725                    730                    735 | 2256 |
| agg cct gca agg gca aaa gtc tcg tgg tac cat ttt cag cgt ctt gga<br>Arg Pro Ala Arg Ala Lys Val Ser Trp Tyr His Phe Gln Arg Leu Gly<br>740                    745                    750 | 2304 |
| att cga gtc gaa gta gtt cca cgt gtt gaa cag gct cta cat tat ctg<br>Ile Arg Val Glu Val Val Pro Arg Val Glu Gln Ala Leu His Tyr Leu<br>         755                    760                    765 | 2352 |
| aag att ggt act acc act gtg aat atg ata ctc ata gag caa gaa ata<br>Lys Ile Gly Thr Thr Thr Val Asn Met Ile Leu Ile Glu Gln Glu Ile<br>770                    775                    780 | 2400 |
| | 2400 |
| aag att ggt act acc act gtg aat atg ata ctc ata gag caa gaa ata<br>Lys Ile Gly Thr Thr Thr Val Asn Met Ile Leu Ile Glu Gln Glu Ile<br>785                    790                    795                    800 | 2400 |
| tgg aat agg gaa gca gat gat ttc att aaa aag cta cag aaa gac cct<br>Trp Asn Arg Glu Ala Asp Asp Phe Ile Lys Lys Leu Gln Lys Asp Pro<br>                    805                    810                    815 | 2448 |
| ctt ttc ctt tct cct aag ttg att ttg tta gca aac tca gta gaa tcg<br>Leu Phe Leu Ser Pro Lys Leu Ile Leu Leu Ala Asn Ser Val Glu Ser<br>820                    825                    830 | 2496 |
| tca ata tca gag gct tta tgc acc ggt ata gat cct cca ata gtg ata<br>Ser Ile Ser Glu Ala Leu Cys Thr Gly Ile Asp Pro Pro Ile Val Ile<br>         835                    840                    845 | 2544 |
| gtg aaa cca ttg agg gcg agt atg cta gca gca act ttg cag agg gga<br>Val Lys Pro Leu Arg Ala Ser Met Leu Ala Ala Thr Leu Gln Arg Gly<br>850                    855                    860 | 2592 |
| ttg ggt att gga atc aga gaa cca cct caa cac aag gga cct cct gct<br>Leu Gly Ile Gly Ile Arg Glu Pro Pro Gln His Lys Gly Pro Pro Ala<br>865                  870                    875                    880 | 2640 |
| ttg att ctc agg aat ctt ctc ctt ggt aga aaa att tta atc gtg gat<br>Leu Ile Leu Arg Asn Leu Leu Leu Gly Arg Lys Ile Leu Ile Val Asp<br>                    885                    890                    895 | 2688 |
| gat aac aac gta aac ctc aga gtg gca gcg gga gct ctg aaa aag tac<br>Asp Asn Asn Val Asn Leu Arg Val Ala Ala Gly Ala Leu Lys Lys Tyr<br>900                    905                    910 | 2736 |
| gga gct gat gtg gtc tgc gct gag agt ggg ata aag gca atc tca ttg<br>Gly Ala Asp Val Val Cys Ala Glu Ser Gly Ile Lys Ala Ile Ser Leu<br>         915                    920                    925 | 2784 |
| ctt aag cca cct cac gag ttt gat gct tgc ttc atg gac att cag atg<br>Leu Lys Pro Pro His Glu Phe Asp Ala Cys Phe Met Asp Ile Gln Met<br>930                    935                    940 | 2832 |
| cca gaa atg gat gga ttt gaa gct aca agg aga ata cga gat atg gaa<br>Pro Glu Met Asp Gly Phe Glu Ala Thr Arg Arg Ile Arg Asp Met Glu<br>945                    950                    955                    960 | 2880 |
| gag gag atg aac aag aga ata aag aat ggg gag gct ttg ata gta gag<br>Glu Glu Met Asn Lys Arg Ile Lys Asn Gly Glu Ala Leu Ile Val Glu<br>                    965                    970                    975 | 2928 |
| aac ggt aac aaa aca agc tgg cat ctt ccg gta tta gca atg acg gca<br>Asn Gly Asn Lys Thr Ser Trp His Leu Pro Val Leu Ala Met Thr Ala<br>980                    985                    990 | 2976 |
| gat gtg atc caa gca acg cat gag gaa tgt ctg aag tgt gga atg gat<br>Asp Val Ile Gln Ala Thr His Glu Glu Cys Leu Lys Cys Gly Met Asp<br>         995                    1000                  1005 | 3024 |
| ggg tat gta tca aaa cca ttt gaa gca gag cag ctg tac agg gaa gtt<br>Gly Tyr Val Ser Lys Pro Phe Glu Ala Glu Gln Leu Tyr Arg Glu Val<br>    1010                    1015                    1020 | 3072 |
| tct cgc ttt ttc aat tcg cct tca gat aca gaa tca taa | 3111 |

Ser Arg Phe Phe Asn Ser Pro Ser Asp Thr Glu Ser
1025                1030                1035

<210> SEQ ID NO 4
<211> LENGTH: 1036
<212> TYPE: PRT
<213> ORGANISM: Arabidopsis thaliana

<400> SEQUENCE: 4

Met Ser Leu Phe His Val Leu Gly Phe Gly Val Lys Ile Gly His Leu
 1               5                  10                  15

Phe Trp Met Leu Cys Cys Trp Phe Val Ser Trp Phe Val Asp Asn Gly
                20                  25                  30

Ile Glu Asp Lys Ser Gly Leu Leu Val Gly Ser Val Gly Asp Leu Glu
            35                  40                  45

Lys Thr Lys Met Thr Thr Leu Lys Lys Asn Lys Met Trp Phe Trp
     50                  55                  60

Asn Lys Ile Ser Ser Ser Gly Leu Lys Ile Pro Ser Phe Ser Tyr Gln
 65                  70                  75                  80

Phe Leu Gly Ser Val Lys Phe Asn Lys Ala Trp Trp Arg Lys Leu Val
                85                  90                  95

Val Val Trp Val Val Phe Trp Val Leu Val Ser Ile Trp Thr Phe Trp
            100                 105                 110

Tyr Phe Ser Ser Gln Ala Met Glu Lys Arg Lys Glu Thr Leu Ala Ser
        115                 120                 125

Met Cys Asp Glu Arg Ala Arg Met Leu Gln Asp Gln Phe Asn Val Ser
130                 135                 140

Met Asn His Val Gln Ala Met Ser Ile Leu Ile Ser Thr Phe His His
145                 150                 155                 160

Gly Lys Ile Pro Ser Ala Ile Asp Gln Arg Thr Phe Ser Glu Tyr Thr
                165                 170                 175

Asp Arg Thr Ser Phe Glu Arg Pro Leu Thr Ser Gly Val Ala Tyr Ala
            180                 185                 190

Met Arg Val Leu His Ser Glu Arg Glu Phe Glu Arg Gln Gln Gly
        195                 200                 205

Trp Thr Ile Arg Lys Met Tyr Ser Leu Glu Gln Asn Pro Val His Lys
    210                 215                 220

Asp Asp Tyr Asp Leu Glu Ala Leu Glu Pro Ser Pro Val Gln Glu Glu
225                 230                 235                 240

Tyr Ala Pro Val Ile Phe Ala Gln Asp Thr Val Ser His Val Val Ser
                245                 250                 255

Leu Asp Met Leu Ser Gly Lys Glu Asp Arg Glu Asn Val Leu Arg Ala
            260                 265                 270

Arg Ser Ser Gly Lys Gly Val Leu Thr Ala Pro Phe Pro Leu Ile Lys
        275                 280                 285

Thr Asn Arg Leu Gly Val Ile Leu Thr Phe Ala Val Tyr Lys Arg Asp
    290                 295                 300

Leu Pro Ser Asn Ala Thr Pro Lys Glu Arg Ile Glu Ala Thr Asn Gly
305                 310                 315                 320

Tyr Leu Gly Gly Val Phe Asp Ile Glu Ser Leu Val Glu Asn Leu Leu
                325                 330                 335

Gln Gln Leu Ala Ser Lys Gln Thr Ile Leu Val Asn Val Tyr Asp Ile
            340                 345                 350

Thr Asn His Ser Gln Pro Ile Ser Met Tyr Gly Thr Asn Val Ser Ala
        355                 360                 365

-continued

```
Asp Gly Leu Glu Arg Val Ser Pro Leu Ile Phe Gly Asp Pro Leu Arg
    370                 375                 380

Lys His Glu Met Arg Cys Arg Phe Lys Gln Lys Pro Pro Trp Pro Val
385                 390                 395                 400

Leu Ser Met Val Thr Ser Phe Gly Ile Leu Val Ile Ala Leu Leu Val
                    405                 410                 415

Ala His Ile Ile His Ala Thr Val Ser Arg Ile His Lys Val Glu Glu
                420                 425                 430

Asp Cys Asp Lys Met Lys Gln Leu Lys Lys Ala Glu Ala Ala Asp
        435                 440                 445

Val Ala Lys Ser Gln Phe Leu Ala Thr Val Ser His Glu Ile Arg Thr
    450                 455                 460

Pro Met Asn Gly Val Leu Gly Met Leu His Met Leu Met Asp Thr Glu
465                 470                 475                 480

Leu Asp Val Thr Gln Gln Asp Tyr Val Arg Thr Ala Gln Ala Ser Gly
                    485                 490                 495

Lys Ala Leu Val Ser Leu Ile Asn Glu Val Leu Asp Gln Ala Lys Ile
                500                 505                 510

Glu Ser Gly Lys Leu Glu Leu Glu Glu Val Arg Phe Asp Leu Arg Gly
    515                 520                 525

Ile Leu Asp Asp Val Leu Ser Leu Phe Ser Ser Lys Ser Gln Gln Lys
    530                 535                 540

Gly Val Glu Leu Ala Val Tyr Ile Ser Asp Arg Val Pro Asp Met Leu
545                 550                 555                 560

Ile Gly Asp Pro Gly Arg Phe Arg Gln Ile Leu Thr Asn Leu Met Gly
                565                 570                 575

Asn Ser Ile Lys Phe Thr Glu Lys Gly His Ile Phe Val Thr Val His
                580                 585                 590

Leu Val Asp Glu Leu Phe Glu Ser Ile Asp Gly Glu Thr Ala Ser Ser
    595                 600                 605

Pro Glu Ser Thr Leu Ser Gly Leu Pro Val Ala Asp Arg Gln Arg Ser
    610                 615                 620

Trp Glu Asn Phe Lys Ala Phe Ser Ser Asn Gly His Arg Ser Phe Glu
625                 630                 635                 640

Pro Ser Pro Pro Asp Ile Asn Leu Ile Val Ser Val Glu Asp Thr Gly
                645                 650                 655

Val Gly Ile Pro Val Glu Ala Gln Ser Arg Ile Phe Thr Pro Phe Met
                660                 665                 670

Gln Val Gly Pro Ser Ile Ser Arg Thr His Gly Gly Thr Gly Ile Gly
    675                 680                 685

Leu Ser Ile Ser Lys Cys Leu Val Gly Leu Met Lys Gly Glu Ile Gly
    690                 695                 700

Phe Ser Ser Thr Pro Lys Val Gly Ser Thr Phe Thr Phe Thr Ala Val
705                 710                 715                 720

Phe Ser Asn Gly Met Gln Pro Ala Glu Arg Lys Asn Asp Asn Gln
                725                 730                 735

Pro Ile Phe Ser Glu Phe Arg Gly Met Lys Ala Val Val Asp His
                740                 745                 750

Arg Pro Ala Arg Ala Lys Val Ser Trp Tyr His Phe Gln Arg Leu Gly
            755                 760                 765

Ile Arg Val Glu Val Val Pro Arg Val Glu Gln Ala Leu His Tyr Leu
    770                 775                 780
```

```
Lys Ile Gly Thr Thr Thr Val Asn Met Ile Leu Ile Glu Gln Glu Ile
785                 790                 795                 800

Trp Asn Arg Glu Ala Asp Phe Ile Lys Lys Leu Gln Lys Asp Pro
        805                 810                 815

Leu Phe Leu Ser Pro Lys Leu Ile Leu Leu Ala Asn Ser Val Glu Ser
            820                 825                 830

Ser Ile Ser Glu Ala Leu Cys Thr Gly Ile Asp Pro Pro Ile Val Ile
        835                 840                 845

Val Lys Pro Leu Arg Ala Ser Met Leu Ala Thr Leu Gln Arg Gly
    850                 855                 860

Leu Gly Ile Gly Ile Arg Glu Pro Pro Gln His Lys Gly Pro Pro Ala
865                 870                 875                 880

Leu Ile Leu Arg Asn Leu Leu Leu Gly Arg Lys Ile Leu Ile Val Asp
                885                 890                 895

Asp Asn Asn Val Asn Leu Arg Val Ala Ala Gly Ala Leu Lys Lys Tyr
            900                 905                 910

Gly Ala Asp Val Val Cys Ala Glu Ser Gly Ile Lys Ala Ile Ser Leu
        915                 920                 925

Leu Lys Pro Pro His Glu Phe Asp Ala Cys Phe Met Asp Ile Gln Met
    930                 935                 940

Pro Glu Met Asp Gly Phe Glu Ala Thr Arg Arg Ile Arg Asp Met Glu
945                 950                 955                 960

Glu Glu Met Asn Lys Arg Ile Lys Asn Gly Glu Ala Leu Ile Val Glu
                965                 970                 975

Asn Gly Asn Lys Thr Ser Trp His Leu Pro Val Leu Ala Met Thr Ala
            980                 985                 990

Asp Val Ile Gln Ala Thr His Glu Glu Cys Leu Lys Cys Gly Met Asp
        995                1000                1005

Gly Tyr Val Ser Lys Pro Phe Glu Ala Glu Gln Leu Tyr Arg Glu Val
    1010                1015                1020

Ser Arg Phe Phe Asn Ser Pro Ser Asp Thr Glu Ser
1025                1030                1035

<210> SEQ ID NO 5
<211> LENGTH: 3174
<212> TYPE: DNA
<213> ORGANISM: Arabidopsis thaliana
<220> FEATURE:
<221> NAME/KEY: CDS
<222> LOCATION: (1)..(3174)

<400> SEQUENCE: 5 atg aac tgg gca ctc aac aat cat caa gaa gaa gaa gaa gag cca cga      48
Met Asn Trp Ala Leu Asn Asn His Gln Glu Glu Glu Glu Glu Pro Arg
 1               5                  10                  15 aga att gaa att tct gat tcc gag tca cta gaa aac ttg aaa agc agc      96
Arg Ile Glu Ile Ser Asp Ser Glu Ser Leu Glu Asn Leu Lys Ser Ser
             20                  25                  30 gat ttt tat caa ctg ggt ggt ggt ggt gct ctg aat tcg tca gaa aag     144
Asp Phe Tyr Gln Leu Gly Gly Gly Gly Ala Leu Asn Ser Ser Glu Lys
         35                  40                  45 ccg aga aag atc gat ttt tgg cgt tcg ggg ttg atg ggt ttt gcg aag     192
Pro Arg Lys Ile Asp Phe Trp Arg Ser Gly Leu Met Gly Phe Ala Lys
     50                  55                  60 atg cag cag cag caa cag ctt cag cat tca gtg gcg gtg aag atg aac     240
Met Gln Gln Gln Gln Gln Leu Gln His Ser Val Ala Val Lys Met Asn
 65                  70                  75                  80
```

```
                                                   -continued aat aat aat aat aac gat cta atg ggt aat aaa aaa ggg tca act ttc        288
Asn Asn Asn Asn Asn Asp Leu Met Gly Asn Lys Lys Gly Ser Thr Phe
                85                  90                  95 ata caa gaa cat cga gca ttg tta cca aaa gct ttg att ctg tgg atc        336
Ile Gln Glu His Arg Ala Leu Leu Pro Lys Ala Leu Ile Leu Trp Ile
            100                 105                 110 atc att gtt ggg ttt ata agc agt ggg att tat cag tgg atg gat gat        384
Ile Ile Val Gly Phe Ile Ser Ser Gly Ile Tyr Gln Trp Met Asp Asp
        115                 120                 125 gct aat aag att aga agg gaa gag gtt ttg gtc agc atg tgt gat caa        432
Ala Asn Lys Ile Arg Arg Glu Glu Val Leu Val Ser Met Cys Asp Gln
    130                 135                 140 aga gct aga atg ttg cag gat caa ttt agt gtt agt gtt aat cat gtt        480
Arg Ala Arg Met Leu Gln Asp Gln Phe Ser Val Ser Val Asn His Val
145                 150                 155                 160 cat gct ttg gct att ctc gtc tcc act ttt cat tac cac aag aac cct        528
His Ala Leu Ala Ile Leu Val Ser Thr Phe His Tyr His Lys Asn Pro
                165                 170                 175 tct gca att gat cag gag aca ttt gcg gag tac acg gca aga aca gca        576
Ser Ala Ile Asp Gln Glu Thr Phe Ala Glu Tyr Thr Ala Arg Thr Ala
            180                 185                 190 ttt gag aga ccg tta cta agt gga gtg gct tat gct gaa aaa gtt gtg        624
Phe Glu Arg Pro Leu Leu Ser Gly Val Ala Tyr Ala Glu Lys Val Val
        195                 200                 205 aat ttt gag agg gag atg ttt gag cgg cag cac aat tgg gtt ata aag        672
Asn Phe Glu Arg Glu Met Phe Glu Arg Gln His Asn Trp Val Ile Lys
    210                 215                 220 aca atg gat aga gga gag cct tca ccg gtt agg gat gag tat gct cct        720
Thr Met Asp Arg Gly Glu Pro Ser Pro Val Arg Asp Glu Tyr Ala Pro
225                 230                 235                 240 gtt ata ttc tct caa gat agt gtc tct tac ctt gag tca ctc gat atg        768
Val Ile Phe Ser Gln Asp Ser Val Ser Tyr Leu Glu Ser Leu Asp Met
                245                 250                 255 atg tca ggc gag gag gat cgt gag aat att ttg cga gct aga gaa acc        816
Met Ser Gly Glu Glu Asp Arg Glu Asn Ile Leu Arg Ala Arg Glu Thr
            260                 265                 270 gga aaa gct gtc ttg act agc cct ttt agg ttg ttg gaa act cac cat        864
Gly Lys Ala Val Leu Thr Ser Pro Phe Arg Leu Leu Glu Thr His His
        275                 280                 285 ctc gga gtt gtg ttg aca ttc cct gtc tac aag tct tct ctt cct gaa        912
Leu Gly Val Val Leu Thr Phe Pro Val Tyr Lys Ser Ser Leu Pro Glu
    290                 295                 300 aat ccg act gtc gaa gag cgt att gca gcc act gca ggg tac ctt ggt        960
Asn Pro Thr Val Glu Glu Arg Ile Ala Ala Thr Ala Gly Tyr Leu Gly
305                 310                 315                 320 ggt gcg ttt gat gtg gag tct cta gtc gag aat tta ctt ggt cag ctt       1008
Gly Ala Phe Asp Val Glu Ser Leu Val Glu Asn Leu Leu Gly Gln Leu
                325                 330                 335 gct ggt aac caa gca ata gtt gtg cat gtg tat gat atc acc aat gca       1056
Ala Gly Asn Gln Ala Ile Val Val His Val Tyr Asp Ile Thr Asn Ala
            340                 345                 350 tca gat cca ctt gtc atg tat ggt aat caa gat gaa gaa gcc gac aga       1104
Ser Asp Pro Leu Val Met Tyr Gly Asn Gln Asp Glu Glu Ala Asp Arg
        355                 360                 365 tct ctc tct cat gag agc aag ctc gat ttt gga gac ccc ttc agg aaa       1152
Ser Leu Ser His Glu Ser Lys Leu Asp Phe Gly Asp Pro Phe Arg Lys
    370                 375                 380 cat aag atg ata tgc agg tac cac caa aag gca cca ata cca ttg aat       1200
His Lys Met Ile Cys Arg Tyr His Gln Lys Ala Pro Ile Pro Leu Asn
385                 390                 395                 400
```

```
                                                                -continued gtg ctc aca act gtg cca ttg ttc ttt gcg att ggt ttc ttg gtg ggt     1248
Val Leu Thr Thr Val Pro Leu Phe Phe Ala Ile Gly Phe Leu Val Gly
                    405                 410                 415 tat ata ctg tat ggt gca gct atg cac ata gta aaa gtc gaa gat gat     1296
Tyr Ile Leu Tyr Gly Ala Ala Met His Ile Val Lys Val Glu Asp Asp
                420                 425                 430 ttc cat gaa atg caa gag ctt aaa gtg cga gca gaa gct gct gat gtc     1344
Phe His Glu Met Gln Glu Leu Lys Val Arg Ala Glu Ala Ala Asp Val
            435                 440                 445 gct aaa tcg cag ttt ctt gct acc gtg tct cac gag atc agg aca cca     1392
Ala Lys Ser Gln Phe Leu Ala Thr Val Ser His Glu Ile Arg Thr Pro
        450                 455                 460 atg aat ggc att ctc gga atg ctt gct atg ctc cta gat aca gaa cta     1440
Met Asn Gly Ile Leu Gly Met Leu Ala Met Leu Leu Asp Thr Glu Leu
465                 470                 475                 480 agc tcg aca cag aga gat tac gct caa acc gct caa gta tgt ggt aaa     1488
Ser Ser Thr Gln Arg Asp Tyr Ala Gln Thr Ala Gln Val Cys Gly Lys
                485                 490                 495 gct ttg att gca ttg ata aat gag gtt ctt gat cgc gcc aag att gaa     1536
Ala Leu Ile Ala Leu Ile Asn Glu Val Leu Asp Arg Ala Lys Ile Glu
                500                 505                 510 gct gga aag ctg gag ttg gaa tca gta cca ttt gat atc cgt tca ata     1584
Ala Gly Lys Leu Glu Leu Glu Ser Val Pro Phe Asp Ile Arg Ser Ile
            515                 520                 525 ttg gat gat gtc ctt tct cta ttc tct gag gag tca agg aac aaa ggc     1632
Leu Asp Asp Val Leu Ser Leu Phe Ser Glu Glu Ser Arg Asn Lys Gly
        530                 535                 540 att gag ctc gcg gtt ttc gtt tca gac aaa gta cca gag ata gtc aaa     1680
Ile Glu Leu Ala Val Phe Val Ser Asp Lys Val Pro Glu Ile Val Lys
545                 550                 555                 560 gga gat tca ggg aga ttt aga cag ata atc ata aac ctt gtt gga aat     1728
Gly Asp Ser Gly Arg Phe Arg Gln Ile Ile Ile Asn Leu Val Gly Asn
                565                 570                 575 tcg gtt aaa ttc aca gag aaa gga cat atc ttt gtt aaa gtc cat ctt     1776
Ser Val Lys Phe Thr Glu Lys Gly His Ile Phe Val Lys Val His Leu
                580                 585                 590 gcg gaa caa tca aaa gat gaa tct gaa ccg aaa aat gca ttg aat ggt     1824
Ala Glu Gln Ser Lys Asp Glu Ser Glu Pro Lys Asn Ala Leu Asn Gly
            595                 600                 605 gga gtg tct gaa gaa atg atc gtt gtt tcc aaa cag tca agt tac aac     1872
Gly Val Ser Glu Glu Met Ile Val Val Ser Lys Gln Ser Ser Tyr Asn
        610                 615                 620 aca ttg agc ggt tac gaa gct gct gat ggt cgg aat agc tgg gat tca     1920
Thr Leu Ser Gly Tyr Glu Ala Ala Asp Gly Arg Asn Ser Trp Asp Ser
625                 630                 635                 640 ttc aag cat ttg gtc tct gag gag cag tca tta tcg gag ttt gat att     1968
Phe Lys His Leu Val Ser Glu Glu Gln Ser Leu Ser Glu Phe Asp Ile
                645                 650                 655 tct agc aat gtt agg ctt atg gtt tca atc gaa gac acg ggt att gga     2016
Ser Ser Asn Val Arg Leu Met Val Ser Ile Glu Asp Thr Gly Ile Gly
                660                 665                 670 atc cct tta gtt gca caa ggc cgt gtg ttt atg ccg ttt atg caa gca     2064
Ile Pro Leu Val Ala Gln Gly Arg Val Phe Met Pro Phe Met Gln Ala
            675                 680                 685 gat agc tcg act tca aga aac tat gga ggt act ggt att ggt ttg agt     2112
Asp Ser Ser Thr Ser Arg Asn Tyr Gly Gly Thr Gly Ile Gly Leu Ser
        690                 695                 700 ata agc aag tgt ctt gtt gaa ctt atg cgt ggt cag ata aat ttc ata     2160
Ile Ser Lys Cys Leu Val Glu Leu Met Arg Gly Gln Ile Asn Phe Ile
```

```
                                        -continued
705                 710                 715                 720
agc cgg cct cat att gga agc acg ttc tgg ttc acg gct gtt tta gag     2208
Ser Arg Pro His Ile Gly Ser Thr Phe Trp Phe Thr Ala Val Leu Glu
            725                 730                 735 aaa tgc gat aaa tgc agt gcg att aac cat atg aag aaa cct aat gtg     2256
Lys Cys Asp Lys Cys Ser Ala Ile Asn His Met Lys Lys Pro Asn Val
            740                 745                 750 gaa cac ttg cct tct act ttt aaa gga atg aaa gct ata gtt gtt gat     2304
Glu His Leu Pro Ser Thr Phe Lys Gly Met Lys Ala Ile Val Val Asp
            755                 760                 765 gct aag cct gtt aga gct gct gtg act aga tac cat atg aaa aga ctc     2352
Ala Lys Pro Val Arg Ala Ala Val Thr Arg Tyr His Met Lys Arg Leu
        770                 775                 780 gga atc aat gtt gat gtc gtg aca agt ctc aaa acc gct gtt gtt gca     2400
Gly Ile Asn Val Asp Val Val Thr Ser Leu Lys Thr Ala Val Val Ala
785                 790                 795                 800 gct gct gcg ttt gaa aga aac ggt tct cct ctc cca aca aaa ccg caa     2448
Ala Ala Ala Phe Glu Arg Asn Gly Ser Pro Leu Pro Thr Lys Pro Gln
                805                 810                 815 ctt gat atg atc tta gta gag aaa gat tca tgg att tca act gaa gat     2496
Leu Asp Met Ile Leu Val Glu Lys Asp Ser Trp Ile Ser Thr Glu Asp
            820                 825                 830 aat gac tca gag att cgt tta ttg aat tca aga acc aac gga aac gtt     2544
Asn Asp Ser Glu Ile Arg Leu Leu Asn Ser Arg Thr Asn Gly Asn Val
            835                 840                 845 cat cac aag tct ccg aaa cta gct cta ttc gca aca aac atc aca aat     2592
His His Lys Ser Pro Lys Leu Ala Leu Phe Ala Thr Asn Ile Thr Asn
        850                 855                 860 tcg gag ttc gac aga gct aaa tcc gca gga ttt gca gat acg gta ata     2640
Ser Glu Phe Asp Arg Ala Lys Ser Ala Gly Phe Ala Asp Thr Val Ile
865                 870                 875                 880 atg aaa ccg tta aga gca agc atg att ggg gcg tgt ctg caa caa gtt     2688
Met Lys Pro Leu Arg Ala Ser Met Ile Gly Ala Cys Leu Gln Gln Val
                885                 890                 895 ctc gag ctg aga aaa aca aga caa caa cat cca gaa gga tca tca ccc     2736
Leu Glu Leu Arg Lys Thr Arg Gln Gln His Pro Glu Gly Ser Ser Pro
            900                 905                 910 gca act ctc aag agc ttg ctt aca ggg aag aag att ctt gtg gtt gat     2784
Ala Thr Leu Lys Ser Leu Leu Thr Gly Lys Lys Ile Leu Val Val Asp
        915                 920                 925 gat aat ata gtt aac agg aga gta gct gca gga gct ctc aag aaa ttt     2832
Asp Asn Ile Val Asn Arg Arg Val Ala Ala Gly Ala Leu Lys Lys Phe
930                 935                 940 gga gca gaa gtg gtt tgt gca gag agt ggt caa gtt gct ttg ggt ttg     2880
Gly Ala Glu Val Val Cys Ala Glu Ser Gly Gln Val Ala Leu Gly Leu
945                 950                 955                 960 ctt cag att cca cac act ttc gat gct tgc ttc atg gat att caa atg     2928
Leu Gln Ile Pro His Thr Phe Asp Ala Cys Phe Met Asp Ile Gln Met
                965                 970                 975 cca cag atg gac gga ttt gaa gca act cgt cag ata aga atg atg gag     2976
Pro Gln Met Asp Gly Phe Glu Ala Thr Arg Gln Ile Arg Met Met Glu
            980                 985                 990 aag gaa gct aaa gag aag acg aat ctc gaa tgg cat tta ccg att cta     3024
Lys Glu Ala Lys Glu Lys Thr Asn Leu Glu Trp His Leu Pro Ile Leu
        995                 1000                1005 gcg atg act gcg gat gtg ata cac gcg acc tac gag gaa tgt ctg aaa     3072
Ala Met Thr Ala Asp Val Ile His Ala Thr Tyr Glu Glu Cys Leu Lys
    1010                1015                1020 agt ggg atg gat ggt tac gtc tcc aaa cct ttt gaa gaa gag aat ctc     3120
```

```
Ser Gly Met Asp Gly Tyr Val Ser Lys Pro Phe Glu Glu Asn Leu
1025                1030                1035                1040 tat aaa tcc gtt gcc aaa tca ttc aaa cct aat cct atc tca cct tcg      3168
Tyr Lys Ser Val Ala Lys Ser Phe Lys Pro Asn Pro Ile Ser Pro Ser
            1045                1050                1055 tcg taa                                                              3174
Ser

<210> SEQ ID NO 6
<211> LENGTH: 1057
<212> TYPE: PRT
<213> ORGANISM: Arabidopsis thaliana

<400> SEQUENCE: 6

Met Asn Trp Ala Leu Asn Asn His Gln Glu Glu Glu Glu Pro Arg
 1               5                  10                  15

Arg Ile Glu Ile Ser Asp Ser Glu Ser Leu Glu Asn Leu Lys Ser Ser
                20                  25                  30

Asp Phe Tyr Gln Leu Gly Gly Gly Ala Leu Asn Ser Ser Glu Lys
        35                  40                  45

Pro Arg Lys Ile Asp Phe Trp Arg Ser Gly Leu Met Gly Phe Ala Lys
 50                  55                  60

Met Gln Gln Gln Gln Leu Gln His Ser Val Ala Val Lys Met Asn
 65                  70                  75                  80

Asn Asn Asn Asn Asn Asp Leu Met Gly Asn Lys Lys Gly Ser Thr Phe
                85                  90                  95

Ile Gln Glu His Arg Ala Leu Leu Pro Lys Ala Leu Ile Leu Trp Ile
                100                 105                 110

Ile Ile Val Gly Phe Ile Ser Ser Gly Ile Tyr Gln Trp Met Asp Asp
            115                 120                 125

Ala Asn Lys Ile Arg Arg Glu Glu Val Leu Val Ser Met Cys Asp Gln
130                 135                 140

Arg Ala Arg Met Leu Gln Asp Gln Phe Ser Val Ser Val Asn His Val
145                 150                 155                 160

His Ala Leu Ala Ile Leu Val Ser Thr Phe His Tyr His Lys Asn Pro
                165                 170                 175

Ser Ala Ile Asp Gln Glu Thr Phe Ala Glu Tyr Thr Ala Arg Thr Ala
            180                 185                 190

Phe Glu Arg Pro Leu Leu Ser Gly Val Ala Tyr Ala Glu Lys Val Val
        195                 200                 205

Asn Phe Glu Arg Glu Met Phe Glu Arg Gln His Asn Trp Val Ile Lys
210                 215                 220

Thr Met Asp Arg Gly Glu Pro Ser Pro Val Arg Asp Glu Tyr Ala Pro
225                 230                 235                 240

Val Ile Phe Ser Gln Asp Ser Val Ser Tyr Leu Glu Ser Leu Asp Met
                245                 250                 255

Met Ser Gly Glu Glu Asp Arg Glu Asn Ile Leu Arg Ala Arg Glu Thr
            260                 265                 270

Gly Lys Ala Val Leu Thr Ser Pro Phe Arg Leu Leu Glu Thr His His
        275                 280                 285

Leu Gly Val Val Leu Thr Phe Pro Val Tyr Lys Ser Ser Leu Pro Glu
    290                 295                 300

Asn Pro Thr Val Glu Glu Arg Ile Ala Ala Thr Ala Gly Tyr Leu Gly
305                 310                 315                 320

Gly Ala Phe Asp Val Glu Ser Leu Val Glu Asn Leu Leu Gly Gln Leu
```

-continued

```
                325                 330                 335
Ala Gly Asn Gln Ala Ile Val Val His Val Tyr Asp Ile Thr Asn Ala
            340                 345                 350
Ser Asp Pro Leu Val Met Tyr Gly Asn Gln Asp Glu Glu Ala Asp Arg
        355                 360                 365
Ser Leu Ser His Glu Ser Lys Leu Asp Phe Gly Asp Pro Phe Arg Lys
    370                 375                 380
His Lys Met Ile Cys Arg Tyr His Gln Lys Ala Pro Ile Pro Leu Asn
385                 390                 395                 400
Val Leu Thr Thr Val Pro Leu Phe Phe Ala Ile Gly Phe Leu Val Gly
                405                 410                 415
Tyr Ile Leu Tyr Gly Ala Ala Met His Ile Val Lys Val Glu Asp Asp
            420                 425                 430
Phe His Glu Met Gln Glu Leu Lys Val Arg Ala Glu Ala Ala Asp Val
        435                 440                 445
Ala Lys Ser Gln Phe Leu Ala Thr Val Ser His Glu Ile Arg Thr Pro
    450                 455                 460
Met Asn Gly Ile Leu Gly Met Leu Ala Met Leu Leu Asp Thr Glu Leu
465                 470                 475                 480
Ser Ser Thr Gln Arg Asp Tyr Ala Gln Thr Ala Gln Val Cys Gly Lys
                485                 490                 495
Ala Leu Ile Ala Leu Ile Asn Glu Val Leu Asp Arg Ala Lys Ile Glu
            500                 505                 510
Ala Gly Lys Leu Glu Leu Glu Ser Val Pro Phe Asp Ile Arg Ser Ile
        515                 520                 525
Leu Asp Asp Val Leu Ser Leu Phe Ser Glu Glu Ser Arg Asn Lys Gly
    530                 535                 540
Ile Glu Leu Ala Val Phe Val Ser Asp Lys Val Pro Glu Ile Val Lys
545                 550                 555                 560
Gly Asp Ser Gly Arg Phe Arg Gln Ile Ile Asn Leu Val Gly Asn
                565                 570                 575
Ser Val Lys Phe Thr Glu Lys Gly His Ile Phe Val Lys Val His Leu
            580                 585                 590
Ala Glu Gln Ser Lys Asp Glu Ser Glu Pro Lys Asn Ala Leu Asn Gly
        595                 600                 605
Gly Val Ser Glu Glu Met Ile Val Val Ser Lys Gln Ser Ser Tyr Asn
    610                 615                 620
Thr Leu Ser Gly Tyr Glu Ala Ala Asp Gly Arg Asn Ser Trp Asp Ser
625                 630                 635                 640
Phe Lys His Leu Val Ser Glu Glu Gln Ser Leu Ser Glu Phe Asp Ile
                645                 650                 655
Ser Ser Asn Val Arg Leu Met Val Ser Ile Glu Asp Thr Gly Ile Gly
            660                 665                 670
Ile Pro Leu Val Ala Gln Gly Arg Val Phe Met Pro Phe Met Gln Ala
        675                 680                 685
Asp Ser Ser Thr Ser Arg Asn Tyr Gly Gly Thr Gly Ile Gly Leu Ser
    690                 695                 700
Ile Ser Lys Cys Leu Val Glu Leu Met Arg Gly Gln Ile Asn Phe Ile
705                 710                 715                 720
Ser Arg Pro His Ile Gly Ser Thr Phe Trp Phe Thr Ala Val Leu Glu
                725                 730                 735
Lys Cys Asp Lys Cys Ser Ala Ile Asn His Met Lys Lys Pro Asn Val
            740                 745                 750
```

```
Glu His Leu Pro Ser Thr Phe Lys Gly Met Lys Ala Ile Val Val Asp
            755                 760                 765

Ala Lys Pro Val Arg Ala Ala Val Thr Arg Tyr His Met Lys Arg Leu
        770                 775                 780

Gly Ile Asn Val Asp Val Val Thr Ser Leu Lys Thr Ala Val Val Ala
785                 790                 795                 800

Ala Ala Ala Phe Glu Arg Asn Gly Ser Pro Leu Pro Thr Lys Pro Gln
            805                 810                 815

Leu Asp Met Ile Leu Val Glu Lys Asp Ser Trp Ile Ser Thr Glu Asp
            820                 825                 830

Asn Asp Ser Glu Ile Arg Leu Leu Asn Ser Arg Thr Asn Gly Asn Val
            835                 840                 845

His His Lys Ser Pro Lys Leu Ala Leu Phe Ala Thr Asn Ile Thr Asn
            850                 855                 860

Ser Glu Phe Asp Arg Ala Lys Ser Ala Gly Phe Ala Asp Thr Val Ile
865                 870                 875                 880

Met Lys Pro Leu Arg Ala Ser Met Ile Gly Ala Cys Leu Gln Gln Val
            885                 890                 895

Leu Glu Leu Arg Lys Thr Arg Gln Gln His Pro Glu Gly Ser Ser Pro
        900                 905                 910

Ala Thr Leu Lys Ser Leu Leu Thr Gly Lys Lys Ile Leu Val Val Asp
            915                 920                 925

Asp Asn Ile Val Asn Arg Arg Val Ala Ala Gly Ala Leu Lys Lys Phe
        930                 935                 940

Gly Ala Glu Val Val Cys Ala Glu Ser Gly Gln Val Ala Leu Gly Leu
945                 950                 955                 960

Leu Gln Ile Pro His Thr Phe Asp Ala Cys Phe Met Asp Ile Gln Met
            965                 970                 975

Pro Gln Met Asp Gly Phe Glu Ala Thr Arg Gln Ile Arg Met Met Glu
            980                 985                 990

Lys Glu Ala Lys Glu Lys Thr Asn Leu Glu Trp His Leu Pro Ile Leu
        995                 1000                1005

Ala Met Thr Ala Asp Val Ile His Ala Thr Tyr Glu Glu Cys Leu Lys
    1010                1015                1020

Ser Gly Met Asp Gly Tyr Val Ser Lys Pro Phe Glu Glu Glu Asn Leu
1025                1030                1035                1040

Tyr Lys Ser Val Ala Lys Ser Phe Lys Pro Asn Pro Ile Ser Pro Ser
            1045                1050                1055

Ser

<210> SEQ ID NO 7
<211> LENGTH: 125
<212> TYPE: PRT
<213> ORGANISM: Saccharomyces cerevisiae

<400> SEQUENCE: 7

Glu Thr Ser Val Lys Ile Leu Val Val Glu Asp Asn His Val Asn Gln
1               5                   10                  15

Glu Val Ile Lys Arg Met Leu Asn Leu Glu Gly Ile Glu Asn Ile Glu
                20                  25                  30

Leu Ala Cys Asp Gly Gln Glu Ala Phe Asp Lys Val Lys Glu Leu Thr
            35                  40                  45

Ser Lys Gly Glu Asn Tyr Asn Met Ile Phe Met Asp Val Gln Met Pro
        50                  55                  60
```

```
Lys Val Asp Gly Leu Leu Ser Thr Lys Met Ile Arg Arg Asp Leu Gly
 65                  70                  75                  80

Tyr Thr Ser Pro Ile Val Ala Leu Thr Ala Phe Ala Asp Asp Ser Asn
                 85                  90                  95

Ile Lys Glu Cys Leu Glu Ser Gly Met Asn Gly Phe Leu Ser Lys Pro
            100                 105                 110

Ile Lys Arg Pro Lys Leu Lys Thr Ile Leu Thr Glu Phe
        115                 120                 125

<210> SEQ ID NO 8
<211> LENGTH: 118
<212> TYPE: PRT
<213> ORGANISM: Escherichia coli

<400> SEQUENCE: 8

Asn Asp Asp Met Met Ile Leu Val Val Asp Asp His Pro Ile Asn Arg
  1               5                  10                  15

Arg Leu Leu Ala Asp Gln Leu Gly Ser Leu Gly Tyr Gln Cys Lys Thr
                 20                  25                  30

Ala Asn Asp Gly Val Asp Ala Leu Asn Val Leu Ser Lys Asn His Ile
             35                  40                  45

Asp Ile Val Leu Ser Asp Val Asn Met Pro Asn Met Asp Gly Tyr Arg
     50                  55                  60

Leu Thr Gln Arg Ile Arg Gln Leu Gly Leu Thr Leu Pro Val Ile Gly
 65                  70                  75                  80

Val Thr Ala Asn Ala Leu Ala Glu Glu Lys Gln Arg Cys Leu Glu Ser
                 85                  90                  95

Gly Met Asp Ser Cys Leu Ser Lys Pro Val Thr Leu Asp Val Ile Lys
            100                 105                 110

Gln Ser Leu Thr Leu Tyr
        115

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide primer for PCR

<400> SEQUENCE: 9
tccccgcgga aaatgttctt acggttaggt ag                                    32

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide primer for PCR

<400> SEQUENCE: 10
tcggtcgact tatgattctg tatctgaagg cga                                   33

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide primer for PCR
```

```
<400> SEQUENCE: 11
tcagatatga actgggcact caac                                          24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide primer for PCR

<400> SEQUENCE: 12
ctcaatgctt ttgttccttg actc                                          24

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide primer for PCR

<400> SEQUENCE: 13
accatgaact gggcactcaa caatcatcaa g                                  31

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide primer for PCR

<400> SEQUENCE: 14
ggattacgac gaaggtgaga taggattagg                                    30

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide primer for PCR

<400> SEQUENCE: 15
gatcccagct agctagggcc ctaccgcggg ga                                 32

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide primer for PCR

<400> SEQUENCE: 16
tccccgcgga aaatgttctt acggttaggt ag                                 32

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide primer for PCR
```

```
<400> SEQUENCE: 17
tcggtcgact tatgattctg tatctgaagg cga                          33

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide primer for PCR

<400> SEQUENCE: 18
ctagtccccg cggtagggcc ctagctagct gg                           32

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide primer for PCR

<400> SEQUENCE: 19
tccccgcgga aaatgtctat aacttgtgag c                            31

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide primer for PCR

<400> SEQUENCE: 20
ctagctagct taacaaggtt caaagaatct tgc                          33

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide primer for PCR

<400> SEQUENCE: 21
tccccgcgga aaatgaaagc acgaggtgag agg                          33

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide primer for PCR

<400> SEQUENCE: 22
ctagctagct taacaaggtt caaagaatttt gc                          32
```

ANALYSIS OF AGONIST-ACTIVITY AND ANTAGONIST-ACTIVITY TO CYTOKININ RECEPTOR

BACKGROUND OF THE INVENTION

1. Field of the Invention

The present invention relates to a method for analyzing agonist-activity and antagonist-activity of an examinee to cytokinin receptor.

2. Description of the Related Art

Cytokinins are plant hormones relevant to cell division and differentiation of higher plants and are well-known as very important physiologically active substances having functions of inducing division of cells of higher plants, differentiating the callus and pith to the stems and leaves, ethiolating and defoliating leaves, preventing the falling of fruit, breaking the dominance of the terminal bud and the like [Cytokinins: Chemistry, Activity, and Function, CRC press (1994)]. The substances having cytokinins-like activities are usable as plant growth regulators, for example, fruit-falling preventive agents for fruits such as apple, orange, and the like, plant-falling preventive agents for rice plants, barley, wheat and the like by regulating the height of the plants, and sweetness increasing agents for fruits after harvest.

As a method for finding substances having such cytokinins-like activities, conventionally employed is a method for observing and evaluating the physiological changes by directly spraying examinee substances to plant.

The aforementioned method has problems that it requires to prepare the examinee substances in amounts sufficient to directly spray them to plant and also requires immensely long time to observe and evaluate the growth of the plant and the physiological changes of the plant after spraying of the examinee substances. Therefore, it has been required for a long to develop a variety of methods for quickly finding substances having cytokinins-like activities with small amounts of examinee substances.

SUMMARY OF THE INVENTION

Inventors of the present invention have intensively investigated in such situations and first found protein functioning as a cytokinin receptor and subsequently found it possible to analyze the agonist-activity and the antagonist-activity of examinee substances to a cytokinin receptor by using the cytokinin receptor ("the analysis method") and also it possible to quickly search substances having cytokinins-like activities even in a small amount of examinee substances by employing the analysis method and consequently reached the present invention.

The present invention provides

1: A method for analyzing agonist-activity to a cytokinin receptor, which comprises (1) bringing an examinee substance into contact with a transformed cell into which DNA coding the cytokinin receptor is introduced and
(2) measuring the existence or the quantity of intracellular signal transduction from the cytokinin receptor expressed in the transformed cell.

2: The method according to the above 1, wherein the transformed cell is a cell having a function of directly controlling the cell growth by intracellular signal transduction from the cytokinin receptor and the measurement of the existence or the quantity of the intracellular signal transduction is carried out using the quantity of the cell growth of the transformed cell as an indicator.

3: The method according to the above 1, wherein the transformed cell is a transformed cell generated by introducing DNA coding the cytokinin receptor into a host cell so improved as to have histidine kinase activity lower than the intrinsic histidine kinase activity of the host cell.

4: The method according to the above 1, wherein the transformed cell is a transformed cell generated by introducing DNA coding the cytokinin receptor into a host cell so improved as to have histidine kinase activity lower than the intrinsic histidine kinase activity of the host cell by deleting one or more of histidine kinase.

5: The method according to the above 1, wherein the transformed cell is a transformed cell generated by introducing DNA coding the cytokinin receptor into a host cell having no cytokinin receptor.

6: The method according to the above 1, wherein the transformed cell is yeast.

7: The method according to the above 1, wherein the transformed cell is budding yeast.

8: The method according to the above 1, wherein the DNA coding the cytokinin receptor is any one of DNA coding the cytokinin receptor selected from:

(a) a cytokinin receptor having the amino acid sequence represented by SEQ ID No: 6;
(b) a cytokinin receptor having the amino acid sequence represented by SEQ ID No: 2;
(c) a cytokinin receptor having the amino acid sequence represented by SEQ ID No: 4;
(d) a cytokinin receptor wherein said cytokinin receptor has at least one transmembrane region but less than that in its natural form.
(e) a cytokinin receptor having the amino acid sequence from amino acid number 196 to 1176 among the amino acid sequence represented by SEQ ID No: 2;
(f) a cytokinin receptor having the amino acid sequence from amino acid number 50 to 1176 among the amino acid sequence represented by SEQ ID No: 2;
(g) a cytokinin receptor having the amino acid sequence from amino acid number 32 to 1036 among the amino acid sequence represented by SEQ ID No: 4;
(h) a chimera-type cytokinin receptor comprising extracellular regions of the cytokinin receptor, transmembrane regions of the cytokinin receptor, and histidine kinase regions of the cytokinin receptor, wherein each of the regions is a homogeneous region to one another and receiver regions for the histidine kinase, which are heterogeneous regions to these regions; and
(i) a cytokinin receptor having the amino acid sequence with deletion, substitution, or addition of one or a plurality of amino acids in the amino acid sequence of the cyctokinin receptor of (a), (b), (c), (e), (f), or (g).

9: A method for analyzing antagonist-activity to a cytokinin receptor, which comprises (1) bringing an examinee substance and a substance having agonist-activity to the cytokinin receptor into contact with a transformed cell into which DNA coding the cytokinin receptor is introduced and
(2) measuring the existence or the quantity of intracellular signal transduction from the cytokinin receptor expressed in the transformed cell.

10: The method according to the above 9, wherein the transformed cell is a cell having a function of directly controlling the cell growth by intracellular signal transduction from the cytokinin receptor and the measurement of the existence or the quantity of the intracellular signal transduction is carried out using the quantity of the cell growth of the transformed cell as an indicator.

11: The method according to the above 9, wherein the transformed cell is a transformed cell generated by introducing DNA coding the cytokinin receptor into a host cell so improved as to have histidine kinase activity lower than the intrinsic histidine kinase activity of the host cell.

12: The method according to the above 9, wherein the transformed cell is a transformed cell generated by introducing DNA coding the cytokinin receptor into a host cell so improved as to have histidine kinase activity lower than the intrinsic histidine kinase activity of the host cell by deleting one or more of histidine kinase.

13: The method according to the above 9, wherein the transformed cell is a transformed cell generated by introducing DNA coding the cytokinin receptor into a host cell having no cytokinin receptor.

14: The method according to the above 9, wherein the transformed cell is yeast.

15: The method according to the above 9, wherein the transformed cell is budding yeast.

16: The method according to the above 9, wherein the DNA coding the cytokinin receptor is any one of DNA coding the cytokinin receptor selected from:
(a) a cytokinin receptor having the amino acid sequence represented by SEQ ID No: 6;
(b) a cytokinin receptor having the amino acid sequence represented by SEQ ID No: 2;
(c) a cytokinin receptor having the amino acid sequence represented by SEQ ID No: 4;
(d) a cytokinin receptor wherein said cytokinin receptor has at least one transmembrane region but less than that in its natural form.
(e) a cytokinin receptor having the amino acid sequence from amino acid number 196 to 1176 among the amino acid sequence represented by SEQ ID No: 2;
(f) a cytokinin receptor having the amino acid sequence from amino acid number 50 to 1176 among the amino acid sequence represented by SEQ ID No: 2;
(g) a cytokinin receptor having the amino acid sequence from amino acid number 32 to 1036 among the amino acid sequence represented by SEQ ID No: 4;
(h) a chimera-type cytokinin receptor comprising extracellular regions of the cytokinin receptor, transmembrane regions of the cytokinin receptor, and histidine kinase regions of the cytokinin receptor, wherein each of the regions is a homogeneous region to one another and receiver regions for the histidine kinase, which are heterogeneous regions to these regions; and
(i) a cytokinin receptor having the amino acid sequence with deletion, substitution, or addition of one or a plurality of amino acids in the amino acid sequence of the cyctokinin receptor of (a), (b), (c), (e), (f), or (g).

17: A cytokinin receptor selected from:
(d) a cytokinin receptor wherein said cytokinin receptor has at least one transmembrane region but less than that in its natural form.
(e) a cytokinin receptor having the amino acid sequence from amino acid number 196 to 1176 among the amino acid sequence represented by SEQ ID No: 2;
(f) a cytokinin receptor having the amino acid sequence from amino acid number 50 to 1176 among the amino acid sequence represented by SEQ ID No: 2;
(g) a cytokinin receptor having the amino acid sequence from amino acid number 32 to 1036 among the amino acid sequence represented by SEQ ID No: 4;
(h) a chimera-type cytokinin receptor comprising extracellular regions of the cytokinin receptor, transmembrane regions of the cytokinin receptor, and histidine kinase regions of the cytokinin receptor, wherein each of the regions is a homogeneous region to one another and receiver regions for the histidine kinase, which are heterogeneous regions to these regions; and
(i) a cytokinin receptor having the amino acid sequence with deletion, substitution, or addition of one or a plurality of amino acids in the amino acid sequence of the cyctokinin receptor of (e), (f), or (g).

18: DNA coding the cytokinin receptor of the above 17.

19: A transformed cell into which DNA of the above 18 is introduced.

20: A method for detecting agonist-activity to a cytokinin receptor, which comprises evaluating the agonist-activity of two or more different examinee substances to the cytokinin receptor based on the difference obtained by comparison of the existence or the quantity of the intracellular signal transduction in a section where the examinee substances are independently used and measured by the analysis method of the above 1.

21: The method according to the above 20, wherein at least one substance among the two or more different examinee substances is a substance having no agonist-activity to the cytokinin receptor.

22: A method for searching agonist-active substance to a cytokinin receptor, which comprises selecting a substance having agonist-activity to a cytokinin receptor based on the agonist-activity to a cytokinin receptor evaluated by the detecting method of the above 20.

23: A plant growth regulator comprising the substances selected by the searching method of the above 22 as an active ingredient.

24: A method for detecting antagonist-activity to a cytokinin receptor, which comprises evaluating the antagonist-activity of two or more different examinee substances to the cytokinin receptor based on the difference obtained by comparison of the existence or the quantity of the intracellular signal transduction in a section where the examinee substances are independently used and measured by the analysis method of the above 9.

25: The method according to the above 24, wherein at least one substance among the two or more different examinee substances is a substance having no antagonist-activity to the cytokinin receptor.

26: A method for searching antagonist-active substance to a cytokinin receptor, which comprises selecting a substance having antagonist-activity to a cytokinin receptor based on the antagonist-activity to a cytokinin receptor evaluated by the detecting method of the above 24.

27: A plant growth regulator comprising the substances selected by the searching method of the above 26 as an active ingredient.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

DETAILED DESCRIPTION OF THE PREFERRED EMBODIMENTS

Hereinafter, the present invention will be described in detail.

A cytokinin receptor is protein having functions of controlling the propagation and differentiation of cells of higher plants based on the intracellular signal transduction mechanism so-called Two-Component regulatory system (or Histidine to Aspartic acidartic acid phosphorelay system) while being specifically bonded with cytokinins such as purine type cytokinins, e.g. kinetin, zeatin, and the like, and urea type cytokinins, e.g. N-phenyl-N'-(4-pyridyl)urea and the like. The cytokinin receptor to be used in the present invention belongs to the histidine kinase family and is protein composed of extracellular regions, transmembrane regions, histidine kinase regions (regions having histidine kinase activity in the cell and holding Histidine residue to be an active site), and receiver regions (regions having a reception part for phosphate group transfer and holding Aspartic acid residue to be an active site).

Practical examples of the cytokinin receptor are cytokinin receptors having the amino acid sequences represented by SEQ ID Nos: 2, 4, and 6, cytokinin receptors having the amino acid sequences represented by SEQ ID Nos: 2, 4, and 6 wherein one or a plurality of amino acids are deleted, substituted, or added, cytokinin receptors having the amino acid sequences coded with DNA to be hybridized in stringent conditions with DNA having the nucleotide sequences coding the amino acid sequences represented by SEQ ID Nos: 2, 4, and 6, cytokinin receptors of partially transmembrane region-deleted type which will be described later, and chimera-type cytokinin receptors which will be described later, and the like. Incidentally, the phrase, "a plurality of amino acids", means more particularly about 2 to 20 amino acids and for example, 2 to 10 amino acids and 2 to 5 amino acids may be exemplified. Also, the phrase, "the amino acid sequences . . . wherein one or a plurality of amino acids are deleted, substituted, or added", means as examples those having the amino acid sequences of which 80% or higher, preferably 90% or higher, and more preferably 95% or higher are identical with the sequences of the amino acids before the deletion, substitution or addition of amino acids (i.e. amino acid sequence identification of 80% or higher, particularly 90% or higher, and more preferably 95% or higher).

Those phrases, "deletion, substitution or addition of amino acids" or "which 80% or higher . . . are identical" of course include the intracellular processing to which proteins having the amino acid sequences represented by SEQ ID Nos: 2, 4, and 6 are subjected, and the natural variations caused by differences in type of organisms from which the proteins are derived, differences in individual bodies, differences in tissues, and the like.

The phrase, "sequence identification," in the present invention means the identification and homology between two DNA sequences and between two protein sequences. The sequence identification may be determined by comparing two sequences aligned in the optimum states in a region of the sequences of the comparison objects. The DNA or proteins, the comparison objects, may have addition or deletion (e.g. gap and the like) in the optimum alignment of two sequences. Regarding such sequence identification, computation may be performed using, for example, Vector NT1 by producing alignment by utilizing Clusta 1W algorithm [Nucleic Acid Res., 22(22): 4673-4680 (1994)]. Incidentally, the sequence identification may be measured by a sequence analysis soft, practically Vector NT1, GENETYX-MAC and analysis tools provided in public database.

Regarding the phrase, "be hybridized in stringent conditions", the term, hybridization, in this case may be performed, for example, according to a common method described in Molecular Cloning 2nd edition, written by Sambrook J., Frisch E. F., Maniatis T., issued by Cold Spring Harbor Laboratory press. Further, the phrase, "in stringent conditions", means, for example, that a hybrid is formed in a solution of 6×SSC (a solution containing 1.5 M NaCl and 0.15 M trisodium citrate is defined as 10×SSC) at 65° C. and then washed with 1×SSC at a room temperature. The salt concentration in the washing step may be selected, for example, from the condition of 1×SSC at a room temperature (a low stringent condition) to 0.1×SSC at a room temperature (a high stringent condition). The temperature in the washing step may be selected, for example, from a room temperature (a low stringent condition) to 68° C. (a high stringent condition). Further, both of the salt concentration and the temperature may be changed.

(Production of a Transformed Cell into Which DNA Coding a Cytokinin Receptor is Introduced)

A transformed cell into which DNA coding a cytokinin receptor is introduced may be obtained by introducing and expressing DNA coding the cytokinin receptor, that is, DNA having nucleotide sequence coding the amino acid sequence of the cytokinin receptor in a host cell in the following manner. Hereinafter, one example of the method of the production of a transformed cell will be described.

(1) Preparation of cDNA

At first, the total RNA is prepared from plants such as higher plants according to the method described in Molecular Cloning 2nd edition written by J., Sambrook, E., F., Frishch, T., Maniastis.

Concretely, for example, after a part of tissues are sampled from a higher plant such as a monocotyledonous plant, e.g. rice, corn, barley, wheat and the like and a dicotyledonous plant, e.g. tobacco, soybean, Arabidopsis, and the like and then the tissues are frozen in liquefied nitrogen and successively physically milled using a mortar and pestle or the like and after that, either (a) the resulting milled product is mixed with a solution containing guanidine hydrochloride with phenol or SDS with phenol to obtain the total RNA or (b) the resulting milled product is mixed with a solution containing guanidine thiocyanate and further with CsCl and then subjected to centrifugal separation to obtain the total RNA. For the aforementioned process, commercialized kits such as ISOGEN (produced by Nippon Gene Co.), RNeasy Total RNA Purification Kit (produced by QIAGEN Co.), and the like may be employed.

Next, mRNA is prepared from the total RNA. For example, the preparation may be carried out by a method utilizing the hybridization of oligo-dT chains bonded with cellulose or latex and poly-A chains of mRNA. For the operation, for example, commercialized kits such as mRNA Purification Kit (produced by Amersham Pharmacia Co.), OLIGOTEX™ dt30 super (Oligo (dT) latex beads) (produced by Takara Shuzo Co. Ltd.), and the like may be employed.

Further, cDNA is produced using the mRNA (mRNA having poly-A chains) prepared in such a manner. For example, oligo-dT chains or random primers are annealed with mRNA and then reacted with reverse transcriptase to produce cDNA. Further, the cDNA is reacted with, for example, RNaseH, DNA polymerase I to produce double chain cDNA. For the operation, for example, the following commercialized kits may be employed: SMARTTM PCR cDNA Synthesis Kit (produced by Clontech Co.), cDNA Synthesis Kit (produced by Takara Shuzo Co. Ltd.), cDNA Synthesis Kit (produced by Amersham Pharmacia Co.), ZAP-cDNA Synthesis Kit (produced by Stratagene Co.) and the like.

(2) Cloning

The DNA coding the cytokinin receptor may be obtained by a polymerase chain reaction (hereinafter referred as to PCR) from the produced cDNA using, for example, DNA having partial nucleotide sequence of the nucleotide sequence of SEQ ID No: 1, 3 or 5 as a primer or by a hybridization method using DNA having partial nucleotide sequence of the nucleotide sequence of SEQ ID No: 1, 3 or 5 as a probe.

In the case of employing PCR, DNA usable as a primer set is those planned and synthesized based on the nucleotide sequences of about 20 bp to 40 bp, for example, the nucleotide sequences selected respectively from 5'-non-translation regions and 3'-non-translated regions of the nucleotide sequence represented by SEQ ID No: 1, 3, or 5. Examples of the primer set are sets of DNA of nucleotide sequence represented by SEQ ID No: 9 and DNA of nucleotide sequence represented by SEQ ID No: 10. The PCR solution to be used may be prepared by adding reaction solutions instructed by the kit to cDNA 250 ng. The conditions of the PCR may properly be changed depending on the primer set to be used and, for example, concrete conditions include as follows: keeping at 94° C. for 2 minutes, at about 8° C. for 3 minutes, and further repeating 40 cycles each of which comprises steps of keeping at 94° C. for 30 seconds, at 55° C. for 30 seconds, and at 72° C. for 4 minutes; and repeating 5-10 cycles each of which comprises steps of keeping at 94° C. for 5 seconds and at 72° C. for 4 minutes and further repeating about 20 to 40 cycles each of which comprises steps of keeping at 94° C. for 5 seconds and at 70° C. for 4 minutes. For the operation, the following commercialized kits may be, for example, employed: HERCULASE™ (produced by Stratagene), DNA polymerase contained in Advantage cDNA PCR kit (Clontech Co.), TAKARA Ex Taq (Takara Shuzo Co. Ltd.), PLATINUM™ PCR SUPER (thermostable DNA polymerase in a PCR reaction mix) (Lifetech Oriental Co.), and the like.

In the case of employing hybridization, cloning may be carried out according to a method described in, for example, "Cloning and Sequence", Experimental Manual of Plant Biotechnology (edited by Watanabe and Sugiura, Noson Bunka Publisher, 1989)

The probe to be used may be obtained by synthesizing DNA (with the chain length of about 200 nucleotides to 500 nucleotides) having partial nucleotide sequences of the nucleotide sequence represented by SEQ ID No: 1, 3 or 5 and labelling the DNA with radioisotope markers or fluorescent markers according to the known methods using, for example, Random Primed DNA Labelling Kit (Boehringer Co.), Random Primer DNA Labelling Kit Ver. 2 (Takara Shuzo Co., Ltd.), ECL Direct Nucleic Acid Labelling and Detection System (Amersham Pharmacia Co.), Megaprime DNA-labelling system (Amersham Pharmacia Co.) and the like.

Examples of the hybridization conditions include stringent conditions and the following conditions may be exemplified: keeping at 65° C. in the presence of 6×SSC (0.9 M NaCl and 0.09 M trisodium citrate), 5×Denhard's solution [0.1% (w/v) ficoll 400, 0.1% (w/v) polyvinylpyrrolidone, 0.1% BSA], 0.5% (w/v) SDS and 100 µg/ml degenerated salmon sperm DNA or in DIG EASY Hyb solution (Boeringer-Mannheim Co.) containing 100 µg/ml of degenerated salmon sperm DNA, successively keeping at a room temperature for 15 minutes two times in the presence of 1×SSC (0.15 M NaCl and 0.015 M trisodium citrate) and 0.5% (w/v) SDS, and further keeping at 68° C. for 30 minutes in the presence of 0.1×SSC (0.015 M NaCl and 0.0015 M trisodium citrate) and 0.5% SDS.

In order to obtain DNA coding the cytokinin receptor of *Arabidopsis*, PCR is carried out employing TAKARA LA TAQ™ (thermostable polymerase) (Takara Shuzo Co., Ltd.) and using a solution containing cDNA library phage of *Arabidopsis* (about 1,000,000 pfu) as a template and DNA having the nucleotide sequence represented by SEQ ID No: 11 and DNA having the nucleotide sequence represented by SEQ ID No: 12 as a primer set to amplify and obtain DNA to be a probe. The PCR solution to be used may be prepared by adding the reaction solutions instructed by the kit to 250 ng of cDNA library.

The PCR conditions may be as follows: keeping at 94° C. for 2 minutes, at 8° C. for 3 minutes, and further repeating 40 cycles each of which comprises keeping at 94° C. for 30 seconds, at 55° C. for 30 seconds, and at 68° C. for 5 minutes.

Using the amplified and obtained DNA is used as a template, a $^{32}$P-labeled probe may be produced employing Megaprime DNA-labelling system kit (Amersham Pharmacia Co.) and using the reaction solutions instructed by the kit. Using the probe obtained in such a manner, colony hybridization is carried out by a conventional method, practically the hybridization is carried out keeping at 65° C. in the presence of 6×SSC (0.9 M NaCl and 0.09 M trisodium citrate), 5×Denhard's solution [0.1% (w/v) ficoll 400, 0.1% (w/v) polyvinylpyrrolidone, 0.1% BSA], 0.5% (w/v) SDS and 100 µg/ml degenerated salmon sperm DNA or in the DIG EASY Hyb solution (Boeringer-Mannheim Co.) containing 100 µg/ml of degenerated salmon sperm DNA, successively keeping at a room temperature for 15 minutes two times in the presence of 1×SSC (0.15 M NaCl and 0.015 M trisodium citrate) and 0.5% (w/v) SDS, and further keeping at 68° C. for 30 minutes in the presence of 0.1×SSC (0.015 M NaCl and 0.0015 M sodium citrate) and 0.5% SDS to obtain clone hybridized with the probe.

Further, DNA coding the cytokinin receptor may be prepared based on, for example, the nucleotide sequence represented by SEQ ID No: 1, 3 or 5 by chemical synthesis of polynucleotides according to a common method such as phosphite-triester method (Hunkapiller, M. et al., Nature, 310, 105, 1984).

The DNA cording the cytokinin receptor obtained in such a manner may be cloned in a vector by a common method described in, "Molecular Cloning: A Laboratory Manual 2nd edition" (1989), Cold Spring Harbor Laboratory Press; "Current Protocols In Molecular Biology" (1987), John Wiley & Sons, Inc. ISBNO-471-50338-X, and the like. The vector to be used may be, for example, pBlue Script II vector (produced by Stratagene Co.), pUC18/19 vector (produced by Takara Shuzo Co., Ltd.), TA cloning vector (produced by Invitrogen Co.), and the like Incidentally, the nucleotide sequence of cloned DNA may be confirmed by, the Maxam Gilbert method (described in, for example, Maxam, A., M & W. Gilbert, Proc. Natl. Acad. Sci. USA, 74, 560, 1977, and the like), the Sanger method (described in, for example, Sanger, F. & A. R. Coulson, J. Mol. Biol., 94, 441, 1975, Sanger, F. & Nicklen and A. R. Coulson., Proc. Natl. Acad. Sci. USA, 74, 5463, 1977, and the like). For the process, the following commercialized kits may be, for example, employed: Thermo Sequenase II dye terminator cycle sequencing kit (produced by Amersham Pharmacia Co.), Dye Terminator Cycle Sequencing FS Ready Reaction Kit (produced by PE Biosystems Japan Co.), and the like.

(3) Construction of Expression Vector

A expression vector of DNA coding the cytokinin receptor may be constructed according to a common method described in, for example, Molecular Cloning 2nd edition written by J., Sambrook, E., F., Frisch, & T., Maniastis, published by Cold Spring Harbor Laboratory Press.

Usable are vectors to be used in host cells to be transformed, for example, independently replicating vectors which contain genetic information possible to be duplicated in the host cells and further are possible to be isolated from the host cells and purified and may have detectable marker. More practically, in the case of using bacteria such as E. coli as the host cells, for example, Plasmid pUC 119 (produced by Takara Shuzo Co., Ltd.), Phagemid pBluescript II (Stratagene Co.) and the like may be used. In the case of using yeast as the host cells, for example, Plasmid pACT2 (Clontech Co.) and the like may be used. In the case of using plant cells as the host cells, for example, DNA coding the cytokinin receptor may be integrated with Plasmid pBI221 (Clontech Co.) to construct the vectors.

A expression vector possible to express DNA coding the cytokinin receptor in a host cell may be constructed by integrating a promoter with the aforementioned vectors in the upstream of the DNA coding the cytokinin receptor in a binding manner of enabling to function in the host cell. In this case, the phrase, "in a binding manner of enabling to function", means that the promoter and the DNA coding the cytokinin receptor are bonded as to express the DNA coding the cytokinin receptor in the host cell under the control of the promoter. Usable as the promoter possible to function in the host cell in the case of using E. coli as the host cell are, for example, a promoter (lacP) of lactose operon of E. coli, a promoter (trpP) of triptophan operon, a promoter (argP) of arginine operon, a promoter (galP) of galactose operon, a tac-promoter, T7-promoter, T3-promoter, λ-phage promoter, (λ-pL, λ-pR) and the like. In the case of using yeast as the host cell, it may be prepared by a conventional genetic engineering method [described in Method in Enzymology 101 part (p. 192-201) by Ammerer, et. al.] from ADHI promoter (the ADHI promoter is available from the yeast expression vector pAAH5 which contains the ADHI promoter and its terminator and which may be obtained from Washington Research Foundation). The ADHI promoter is included in US patent application number 299,733 of Washington Research Foundation and in the case that it is used for industrial and commercial purposes in USA., it is required to obtain permission from the patent holder. In the case of using a plant cell as the host cell, usable examples are a nopaline synthesis enzyme gene (NOS) promoter, an octopine synthesis enzyme gene (OCT) promoter, a cauliflower mosaic virus (CaMV)-derived 19S promoter, a CaMV-derived 35S promoter and the like.

Further, in the case of integrating DNA coding the cytokinin receptor with a vector previously having a promoter possible to function in a host cell, DNA coding the cytokinin receptor is inserted in the downstream of the promoter and the DNA coding the cytokinin receptor in a manner of enabling to function. For example, the aforementioned plasmid pACT 2 for yeast comprises the ADH1 promoter and therefore, an expression vector possible to express the DNA coding the cytokinin receptor in yeast, for example, CG1945 (Clontech Co.) may be constructed by inserting the DNA coding the cytokinin receptor in the downstream of the ADH1 promoter of the plasmid pACT2.

(4) Production of Transformed Cell

A transformed cell to be used for the present invention may be produced by introducing the constructed expression vector into a host cell by a conventional method. As the host cell to be used for production of the transformed cell, examples are bacteria, yeast, plant cell and the like. As bacteria, examples are bacteria belonging to E. coli, Serratia, Bacillus, Brevibacterium, Corynebacterium, Microbacterium and the like. As yeast, examples are budding yeast and fission yeast. More particularly, examples are yeast belonging to Saccharomyces, Schizosaccharomyces and the like. As plant cell, examples are BY-2 strain, which is a cultured cell of tobacco and BMS strain, which is a cultured cell of corn (Black Mexican Sweet), and the like.

The method for introducing the expression vector into the aforementioned host cell includes a conventional introduction method to be employed corresponding to the host cell to be transformed. For example, in the case of using bacteria as the host cell, the aforementioned expression vector may be introduced into a host cell by employing a conventional introduction method such as a calcium chloride method and an electroporation method described in, "Molecular Cloning" (by J. Sambrook, et. al Cold Spring Harbor 1989). In the case of using yeast as a host cell, the aforementioned expression vector may be introduced into the host cell by employing Yeast transformation kit (produced by Clontech Co.) based on a lithium method. Further, in the case of using a plant cell as a host cell, the aforementioned expression vector may be introduced into the host cell by a conventional introduction method, for example, Agrobacterium infection method (Japanese Examined Patent Application No. 2-58917, Japanese Laid-Open Patent Application No. 60-70080), an electroporation method into a protoplast (Japanese Laid-Open Patent Application No. 60-251887, Japanese Laid-Open Patent Application No. 5-68575), a particle gun method (Japanese Laid-Open Patent Application No. 6-508316, Japanese Laid-Open Patent Application No. 63-258525).

(Transformed Cell in which a Cytokinin Receptor of Partially Transmembrane Region-deleted Type, i.e. a Cytokinin Receptor of a Transmembrane Time Variation Type, is Expressed)

A cytokinin receptor to be used for the present invention includes a cytokinin receptor wherein said cytokinin receptor has at least one transmembrane region but less than that in its natural form (commonly 2 to 4 transmembrane region) (incidentally, in the present invention, such cytokinin receptors are sometimes referred as to cytokinin receptors of partially transmembrane region-deleted type.) In this case, the phrase, "its natural form" means cytokinin receptors having an amino acid sequence most frequently existing among organisms having the similar nomenclature and generally called also as wild-type cytokinin receptor.

Such cytokinin receptor of partially transmembrane regions-deleted type are cytokinin receptors whose transmembrane region structure may be assumed by employing structure assumption software and whose transmembrane regions are partially deleted, for example, in 1 to 2 sites and are less in number than the number of the transmembrane regions of the natural type cytokinin receptors (i.e. natural form).

More particularly, examples of such cytokinin receptors include a cytokinin receptor having the amino acid sequence from amino acid number 196 to 1176 among the amino acid sequence represented by SEQ ID No: 2 (2 transmembrane regions); a cytokinin receptor having the amino acid sequence from amino acid number 50 to 1176 among the amino acid sequence represented by SEQ ID No: 2 (3 transmembrane regions); a cytokinin receptor having the amino acid sequence from amino acid number 32 to 1036 among the amino acid sequence represented by SEQ ID No: 4 (3 transmembrane regions); a cytokinin receptor having the amino acid sequence derived from the amino acid sequences of these cytokinin receptors wherein one or a plurality of amino acids are deleted, substituted or added, for example, cytokinin receptors having the amino acid sequence derived from the amino acid sequences in which one methionine is added to the amino-terminal and the like.

The DNA coding the cytokinin receptor may be constructed as to hold transmembrane regions in a less number than the number of the transmembrane regions of the natural type cytokinin receptors by partially deleting the transmembrane regions by a conventional genetic engineering technique.

Production of the transformed cell in which the DNA coding the cytokinin receptor is introduced may be carried out according to the aforementioned method, "Production of transformed cell in which the DNA coding a cytokinin receptor is introduced".

(Transformed Cell to Express Chimera-type Cytokinin Receptor)

A cytokinin receptor to be used in the present invention also includes a chimera-type cytokinin receptor comprising extracellular regions of the cytokinin receptor, transmembrane regions of the cytokinin receptor, and histidine kinase regions of the cytokinin receptor, wherein each of the regions is a homogeneous region to one another and receiver regions for the histidine kinase, which are heterogeneous regions to these regions.

In the above, histidine kinase regions of the cytokinin receptor means, for example, a region existed at the C-terminal side of a transmembrane regions located in the N-terminal side of the cytokinin receptor, and said region having five conservative motifs which are common to generic histidine kinases as described in Annual Review of Genetics 23:311-336 (1989), Microbiological Reviews 53(4):450-490(1989), Science 262:539-544(1993), and the like. Examples of the region includes a region having the amino acid sequence from amino acid number 587 to 844 among the amino acid sequence represented by SEQ ID No: 2 in a case of AHK2, a region having the amino acid sequence from amino acid number 450 to 700 among the amino acid sequence represented by SEQ ID No: 4 in a case of AHK3 and a region having the amino acid sequence from amino acid number 449 to 714 among the amino acid sequence represented by SEQ ID No: 6 in a case of CRE1.

Receiver regions of the cytokinin receptor means, for example, a region existed between the histidine kinase region and the C-terminal end of the cytokinin receptor, and said region having three conservative motifs which are common to generic histidine kinases as described in Annual Review of Genetics 23:311-336 (1989), Science 262:539-544(1993), and the like. Examples of the region includes a region having the amino acid sequence from amino acid number 891 to 1163 among the amino acid sequence represented by SEQ ID No: 2 in a case of AHK2, a region having the amino acid sequence from amino acid number 746 to 1018 among the amino acid sequence represented by SEQ ID No: 4 in a case of AHK3 and a region having the amino acid sequence from amino acid number 763 to 1038 among the amino acid sequence represented by SEQ ID No: 6 in a case of CRE1.

In addition, a sensor region for cytokinin means, for example, a region which is a part of any of the extracellular regions of the cytokinin receptor, said region existed between a transmembrane region next to the histidine kinase region and a transmembrane region secondary close to the histidine kinase region, and said region have 50% and more identification and homology between three cytokinin receptors of AHK2, AHK3 and CRE1 as described in Plant and Cell Physiology 42(2):231-235(2001) and the like. Examples of the region includes a region having the amino acid sequence from amino acid number 259 to 536 among the amino acid sequence represented by SEQ ID No: 2 in a case of AHK2, a region having the amino acid sequence from amino acid number 120 to 399 among the amino acid sequence represented by SEQ ID No: 4 in a case of AHK3 and a region having the amino acid sequence from amino acid number 132 to 398 among the amino acid sequence represented by SEQ ID No: 6 in a case of CRE1.

The histidine kinase has the following sequence in common in plants, e.g. higher plants, and microorganism. That is, histidine kinase is composed of extracellular regions, transmembrane regions (generally about 2 to 4), histidine kinase regions having histidine kinase activity and holding Histidine residue to be an active site, and receiver regions having a reception part for phosphate group transfer and holding Aspartic acid residue to be an active site. In the chimera-type cytokinin receptor, it is important that the extracellular regions, transmembrane regions, and histidine kinase regions are all derived from the same cytokinin receptor, whereas the receiver regions are derived differently from the former cytokinin receptor.

It is sufficient for the receiver regions of the chimera-type cytokinin receptor to have a function of receiving signals transmitted from the histidine kinase regions and transmitting them to the next step and any may be usable as long as they can complement or improve the intrinsic functions of the receiver regions of histidine kinase comprising the homogeneously derived extracellular regions, transmembrane regions, and histidine kinase regions.

As such receiver regions, usable are, for example, receiver regions of histidine kinase derived from microorganism (e.g. receiver regions of histidine kinase derived from microorganism such as yeast, *E. coli*) and more particularly receiver regions of histidine kinase coded in Sln1 gene derived from budding yeast (e.g. the amino acid sequence represented by SEQ ID No: 7), receiver regions of histidine kinase coded in Chey gene derived from *Salmonella*, receiver regions of histidine kinase coded in RcsC gene, which is a hybrid sensor of *E. coli* [Maeda T, et al. Nature: 369 242-245, (1994): e.g. the amino acid sequence represented by SEQ ID No: 8], receiver regions of histidine kinase coded in Phks gene relevant to cell cycle control of fission yeast [Shieh, J C, et al., Gene Dev. 11, 1008-1022(1997)].

The DNA coding the chimera-type cytokinin receptor may be constructed by respectively producing DNA for each of the extracellular regions of the cytokinin receptor, transmembrane regions of the cytokinin receptor, histidine kinase regions of the cytokinin receptor, and receiver regions for the histidine kinase, joining the DNA by a common genetic engineering technique so as to prevent appearance of any termination codon in the middle while using a proper linker so as to prevent frame shift. Incidentally, the DNA may be produced as one DNA flagment for the extracellular regions of the cytokinin receptor and transmembrane regions of the cytokinin receptor or for extracellular regions of the cytokinin receptor, transmembrane regions of the cytokinin receptor, and histidine kinase regions of the cytokinin receptor.

The polynucleotides coding the aforementioned respective regions may respectively be produced by known methods. For example, in the case of production by PCR, at first, the oligonucleotides (5' side primers) having the nucleotide sequences of 5' terminal regions of respective regions to be amplified and oligonucleotides (3' side primers) having complementary nucleotide sequences to the nucleotide sequences of 3' terminal are designed and synthesized. The primers may be oligonucleotides of about 14 nucleotides to about 35 nucleotides in general and are preferable to contain restriction enzyme recognition sequences usable at the time of ligating the polynucleotides amplified by the PCR to one another or these polynucleotides to vectors in the 5' side of the primers. Then, using the primers and the cDNA library as a template, amplification reactions may be carried out in the common reaction conditions employed for the PCR. As the template to be used in the case of producing the polynucleotides coding the extracellular regions through the transmembrane regions of the cytokinin receptor or the histidine kinase regions of the cytokinin receptor, usable is cDNA library derived from plants such as higher plants. Also as the template to be used in the case of producing the polynucleotides coding the receiver regions of the histidine kinase, usable is cDNA library derived from microorganism prepared by a common method or the total DNA.

The production of the transformed cell in which the DNA coding the chimera-type cytokinin receptor is introduced may be carried out according to the aforementioned, "Production of the transformed cell in which the DNA coding a cytokinin receptor is introduced.".

(Intracellular Signal Transduction System Relevant to Cytokinin)

Measurement of the existence or the quantity of intracellular signal transduction from the cytokinin receptor expressed in the transformed cell produced by the above-described manner in the present invention may be carried out by utilizing the intracellular signal transduction system which the host cell used for production of the transformed cell originally has. The phrase, "the existence or the quantity of intracellular signal transduction" means, for example, the quantity of the cell growth of the transformed cell as an indicator. Alternatively, a regulator and/or a mediator having the intracellular signal transduction function, so-called Two-Component regulatory system, is introduced and expressed in the host cell and the expressed system may be used as the intracellular signal transduction system. Usable as the Two-Component regulatory system, for example, are Two-Component regulatory systems corresponding to 5 types of ethylene receptors; ETR1, ETR2, ERS1, ERS2, and EIN4; which Arabidopsis has [Chang et al., Science 262: 539-544 (1993), Hua et al., Science 269: 1712-1714 (1995), Sakai et al., Plant Cell Physiol 39: 1232-1239 (1998)] and AtHK1 having sensor functions to the osmotic pressure [Urao, Plant ell 11: 1743-1754 (1999)].

As the host cell to be used for production of such a transformed cell, usable are host cells improved as to have histidine kinase activity lower than the intrinsic histidine kinase activity of the host cells. For example, it includes the host cells improved as to have histidine kinase activity lower than the intrinsic histidine kinase activity of the host cell by deleting one or more of histidine kinases. The phrase, "histidine kinase activity lower than" means that the quantity of phosphate group transfer from Histidine residue to be an active site of histidine kinase regions having histidine kinase activity to Aspartic acid residue to be an active site of receiver regions having a reception part has decreased. The state causes change of the quantity of the cell growth, change of the morphology, change of the shape, change of the quantity of the biosynthesis of specific compound, change of the quantity of the metabolism of specific compound in the transformed cell so improved as to have histidine kinase activity lower than the intrinsic histidine kinase activity of the host cell. More particularly, the following strain [Maeda T et al., Nature 369: 242-245 (1994)] may be exemplified: a strain obtained by defecting the Sln1 gene coding the protein having the osmotic pressure sensor function and derived from the budding yeast such as *Saccharomyces cerevisiae* and the like. Since the strain has decreased quantity of the cell growth in the cause of being defected in the histidine kinase existing in Saccharomyces cerevisiae, it can more clearly detect the existence or the quantity of the intracellular signal transduction from the cytokinin receptor expressed in the transformed cell by using the quantity of the cell growth of the transformed cell as an indicator. Further, other preferable example includes a defective strain of the RcsC gene, which is a hybrid sensor derived from *E. coli* and a defective strain of Phks gene relevant to the cell cycle control of fission yeast.

(Method for Analyzing Agonist-activity and Antagonist-activity to a Cytokinin Receptor)

In the method for analyzing agonist-activity to a cytokinin receptor, examples of the first step of bringing an examinee substance into contact with a transformed cell into which DNA coding the cytokinin receptor is introduced include a method for culturing the transformed cell in a culture medium containing the examinee substance. In order to culture the transformed cell, both cultures are usable: liquid-phase culture for culturing the transformed cell in a liquid culture medium and a solid-phase culture for culturing the transformed cell in a solid culture medium produced by adding agar or the like to the liquid culture medium. The concentration of an examinee substance in the culture medium is about 1 nM to about 1 mM and preferably about 10 nM to about 100 µM. The culture time is, for example, 1 hour or longer and 3 days and preferably 25 hours to 2 days. Incidentally, in the case of method for analyzing the agonist-activity to the cytokinin receptor, the culture containing no cytokinin may be used as the culture containing the examinee substance.

In the method for analyzing the antagonist-activity to the cytokinin receptor, examples of the first step of bringing an examinee substance and a substance having the agonist-activity to the cytokinin receptor into contact with a transformed cell into which DNA coding the cytokinin receptor is introduced include a method for culturing the transformed cell in a culture medium containing the examinee substance and a substance having the agonist-activity to the cytokinin receptor. In order to culture the transformed cell, both cultures are usable: liquid-phase culture for culturing the transformed cell in a liquid culture medium and a solid-phase culture for culturing the transformed cell in a solid culture medium produced by adding agar or the like to the liquid culture medium. The concentration of an examinee substance in the culture medium is about 1 nM to about 1 mM and preferably about 10 nM to about 100 µM. The concentration of the substance (e.g. cytokinins such as trans-zeatin, cis-zeatin, benzyl adenine, thidiazuron and the like) having the agonist-activity to the cytokinin receptor is about 1 nM to about 1 mM and preferably about 10 nM to about 100 µM. The culture time is, for example, 1 hour or longer and 3 days and preferably 25 hours to 2 days. Incidentally, in the case of method for analyzing the agonist-activity to the cytokinin receptor, the culture containing no cytokinin may be used as the culture containing the examinee substance.

The agonist-activity or the antagonist-activity of an examinee substance to the cytokinin receptor may be detected by evaluating the agonist-activity of two or more different examinee substances to the cytokinin receptor based on the difference obtained by comparison of the existence and the quantity of the intracellular signal transduction in a region where the examinee substances (preferable is, for example, between at least two or more different examinee substances, at least one has no agonist-activity or antagonist-activity to the cytokinin receptor) are independently used and measured by the aforementioned method for analyzing the agonist-activity or the antagonist-activity to the cytokinin receptor.

More particularly, for example, in the case of using a transformed cell (that is, a transformed cell having a function of directly controlling the cell growth by intracellular signal transduction from the cytokinin receptor) produced using TM182 (Sln1 Δ) [Maeda T et al, Nature 369: 242-245 (1994)], a Sln1 genetically defected strain in which, for example, PTP2 Tyrosine phosphatase gene [Ota et al. Proc. N. A. Sci., USA, 89, 2355-2359 (1992)] is introduced as a host cell, the agonist-activity to the cytokinin receptor may be measured using, as an indicator, the quantity of the cell growth of the transformed cell in a culture medium (an agar culture medium or a liquid culture medium) containing glucose as a carbon source, for example, a DOLU−Gul culture medium. In this case, if into the DOLU+Gul culture medium is added the examinee substance and no substance having the agonist-activity to the cytokinin receptor, the examinee substance found capable of growing the transformed cell can be evaluated as a substance having the agonist-activity to the cytokinin receptor. On the other hand, if into the DOLU+GUL culture medium is added the examinee substance and a substance having the agonist-activity to the cytokinin receptor, the examinee substance found capable of suppressing or inhibiting the growth of the transformed cell can be evaluated as a substance having the antagonist-activity to the cytokinin receptor.

Incidentally, as a blank, investigation may be carried out to find the growth of the transformed cell in a culture medium using galactose as the carbon source in place of glucose, for example, a DOLU+Gal culture medium, independently of the existence of the examinee substance.

Further, in the case of using a transformed cell produced by employing fission yeast, which is a Phks genetically defected strain, as a host cell (that is, a transformed cell having a function of directly controlling the cell growth by the intracellular signal transduction from the cytokinin receptor), the fission pattern of the fission yeast may be observed with a microscope. In this case, if the culture medium contains the examinee substance and no substance having the agonist-activity to the cytokinin receptor, the examinee substance found capable of normal fission and propagation of the transformed cell can be evaluated as a substance having the agonist-activity to the cytokinin receptor. On the other hand, if the culture medium contains an examinee substance and a substance having the agonist-activity to the cytokinin receptor, the examinee substance found capable of suppressing or inhibiting the normal fission and propagation of the transformed cell can be evaluated as a substance having the antagonist-activity to the cytokinin receptor.

Furthermore, in the case of using a transformed cell produced by employing E. coli defective in RcsC gene into which cps-LacZ is introduced as a host cell (that is, a transformed cell having a function of directly controlling reporter gene expression by the intracellular signal transduction from the cytokinin receptor), the X-Gal coloring may be observed in an agar culture medium or a liquid culture medium [Suzuki et al. Plant Cell Physiol 42: 107-113 (2001)]. In this case, if the culture medium contains the examinee substance and no substance having the agonist-activity to the cytokinin receptor, the examinee substance found capable of coloring the transformed cell to be blue can be evaluated as a substance having the agonist-activity to the cytokinin receptor. On the other hand, if the culture medium contains the examinee substance and a substance having the agonist-activity to the cytokinin receptor, the examinee substance found capable of disappearing coloring the blue of the transformed cell can be evaluated as a substance having the antagonist-activity to the cytokinin receptor.

Moreover, an agonist-active substance or an antagonist-active substance to the cytokinin receptor may be searched by selecting substances having the agonist-active substance or the antagonist-active substance to the cytokinin receptor based on the agonist-activity or the antagonist-activity to the cytokinin receptor evaluated by the aforementioned detection methods.

Further, a substance selected by the above described detection methods may be utilized as an active ingredient of a plant growth regulator.

The plants to be the objects to be treated with the aforementioned plant growth regulator are, for example, decorative plants such as flowering plants and ornamental foliage plants; cultivating plants such as crop, vegetable, fruit and the like; fibrous plants; trees; lawn and the like.

The growth regulator is generally mixed with a solid carrier, a liquid carrier, and the like and further, if needed, mixed with a surfactant and other auxiliary agents for the formulation of an agricultural and horticultural agent and formulated in an emulsion agent, a hydrating agent, a suspension agent, a solution agent and the like. In these agricultural and horticultural agents, an agonist-active substance or an antagonist-active substance to the cytokinin receptor may be contained generally in 0.5 to 90% by weight and preferably in 1 to 80% by weight.

Usable as the solid carrier to be used for the formulation of an agricultural and horticultural agent are, for example, clays (kaolinite, kieselguhr, synthesized hydrated silicon oxide, intercalated clays, bentonite, acidic white clay, and the like), talc, other inorganic minerals (sericite, quartz powder, sulfur powder, activated carbon, calcium carbonate, and the like), chemical fertilizers (ammonium sulfate, ammonium phosphate, ammonium nitrate, ammonium chloride, urea, and the like) in finely powdered state or in granular state and usable as the liquid carrier are, for example, water, alcohols (methanol, ethanol and the like), ketones (acetone, methyl ethyl ketone, cylohexanone and the like), aromatic hydrocarbons (toluene, xylene, ethylbenzene, methylnaphthalene and the like), non-aromatic hydrocarbons (hexane, cyclohexane, kerosene and the like), esters (ethyl acetate, butyl acetate and the like), nitrites (acetonitrile, isobutylnitrile and the like), ethers (dioxane, diisopropyl ether and the like), acid amides (dimethylformamide, dimethylacetamide and the like), halohydrocarbons (dichloroethane, trichloroethane and the like), etc.

As the surfactant, usable are, for example, alkylsulfuric acid esters, alkylsulfonic acid salts, alkylarylsulfonic acid salts, alkylaryl ethers and their polyoxyethylene compounds, polyethylene glycols, polyhydric alcohol esters, sugaralcohols and the like.

As other auxiliary agents for the formulation of agricultural and horticultural agents, usable are solidification agents and dispersanst such as casein, gelatin, polysaccharides (starch, acacia, cellulose derivatives, alginic acid and the like), lignin derivatives, bentonite, synthesized water-soluble polymer [poly(vinyl alcohol), poly(vinyl pyrolidone), poly (acrylic acid) and the like] and the like, and stabilizers such as PAP (acidic isopropyl phosphate), BHT (2,6-tert-butyl-4-methylphenol), BHA (2-/3-tert-butyl-4-methoxyphenol), plant oils, mineral oils, aliphatic acids, aliphatic acid esters and the like.

The agonist-active substance or the antagonist-active substance to the cytokinin receptor made to be agricultural and horticultural agents is used as it is or diluted with water to carry out treatment for the stem and leave parts, branch and leave parts, and flower and fruit parts of plants by spraying, for fruits by immersion, and for fruits by application. The plant growth regulator is used for the object plants to carry out the treatment once or a plurality of times.

In the case of using the plant growth regulator for the purpose of suppressing the dropping of fruits, the plant growth regulator is diluted with water and the resulting diluted agent is sprayed to the fruit parts and branch and leave parts before harvest.

In the case of using the plant growth regulator for the purpose of suppressing the ball dropping of cotton, the plant growth regulator is diluted with water and the resulting diluted agent is sprayed to the balls and stem and leave parts of cotton before harvest.

The plant growth regulator may be used for the treatment of growing plants or of plants after harvest.

The application amount of the agonist-active substance or the antagonist-active substance to the cytokinin receptor in an agricultural and horticultural agent is generally 1 to 8000 g per 1 hectare, although it is changed depending on the state of the agricultural and horticultural agent, the timing for the treatment, the method for the treatment, the site for the treatment, and the object plant to be treated. Also in the case of using the plant growth regulator while diluting the agent with water, the concentration of the agent is generally 0.0001 to 1000 mM and preferably 0.001 to 10 mM, although it is changed depending on the state of the agricultural and horticultural agent, the timing for the treatment, the method for the treatment, the site for the treatment, and the object plant to be treated.

Next, hereinafter given are formulation examples of an agricultural and horticultural agent produced from an agonist-active substance or an antagonist-active substance to the cytokinin receptor and used as a plant growth regulator. The parts in the following description of the examples denotes the parts by weight.

Formulation Example 1

A hydrating agent was obtained by sufficiently pulverizing and mixing 50 parts of an agonist-active substance or an antagonist-active substance to the cytokinin receptor, 3 parts of calcium ligninsulfonate, 2 parts of sodium laurylsulfate, and 45 parts of synthesized hydrated silicon oxide.

Formulation Example 2

A hydrating agent was obtained by sufficiently pulverizing and mixing 70 parts of an agonist-active substance or an antagonist-active substance to the cytokinin receptor, 3 parts of calcium ligninsulfonate, 2 parts of sodium laurylsulfate, and 25 parts of synthesized hydrated silicon oxide.

Formulation Example 3

An emulsion agent was obtained by mixing 40 parts of an agonist-active substance or an antagonist-active substance to the cytokinin receptor, 3 parts of polyoxyethylene sorbitane monoolate, 2 parts of CMC (carboxymethyl cellulose), and 52 parts of water and wet-pulverizing the resultant mixture to be 5 μm or smaller in the particle size.

The present invention makes it possible to analyze the agonist-activity and the antagonist-activity to the cytokinin receptor and also makes it possible to quickly search the substances having the agonist-activity and the antagonist-activity to the cytokinin receptor even in a small amount of examinee substances by employing the analysis method.

EXAMPLES

Hereinafter, although the present invention will be described in details with the reference to examples, the present invention is not at all restricted to these examples.

Example 1

Production of *Arabidopsis* cDNA Phage Library for CRE1 Cloning

Seeds of *Arabidopsis thaliana* ecotype Wassilewskija were sterilized with 70% of ethyl alcohol for 1 minute and further sterilized with 1.5% of sodium hypochlorite for 10 minutes. The resulting seeds were well washed with sterilized water and then cultured for 2 weeks in GM culture medium [4.3 g Murashige and Skoog's basal salt mixture, 1% sucrose, 10 ml of 5% MES-KOH (pH 5.7), 0.3% PHYTAGEL™ gellan gum (SIGMA)] to obtain 5 g of the plant. After the plant was frozen in liquified nitrogen and physically milled with a mortar and a pestle. The resulting milled product was mixed with a mixed solution of 10 ml of an extraction buffer [200 mM Tris-HCL (pH 8.5), 100 mM NaCl, 10 mM EDTA, 0.5% SDS, 14 mM β-mercaptoethanol] and 10 g of phenol. After being mixed by a Voltex mixter, the resulting mixture was mixed further with 10 ml of chloroform and vigorously stirred and subjected to centrifugal separation at 10,000 rotation for 20 minutes. The recovered aqueous layer was mixed with LiCl in the concentration to be 2M of the final concentration, left still at −80° C. for 3 hours, thawed and subjected to centrifugal separation at 10,000 rotation for 20 minutes to recover a precipitate. The recovered precipitate was dissolved in 2 ml of TE [10 mM Tris-HCl (pH 8.0), 1 mM EDTA] and then further mixed with 0.2 ml of 3 M sodium acetate (pH 5.2) and 5 ml ethanol and subjected to centrifugal separation to recover RNA as a precipitate. Further, the precipitate (RNA) was subjected to treatment with OLIGOTEX™ dt30 super (oligo d(T) latex beads) (Nippon Rosh Co.) to extract RNA integrated with polyA.

The production of phage cDNA library from the extracted RNA integrated with polyA was carried out employing ZAP-cDNAR Synthesis Kit (Stratagene Co.) according to the instruction. The potency of the produced phage cDNA library was 500,000 PFU.

Example 2

Production of DNA Probe of CRE1

The PCR was carried out employing TAKARA LA Taq™ (Takara Shuzo Co., Ltd.) and using a phage solution (about 1,000,000 PFU) of the phage cDNA library produced in the example 1 as a template and DNA having the nucleotide sequence represented by SEQ ID No: 11 and DNA having the nucleotide sequence represented by SEQ ID No: 12 as the primers to amplify DNA. The procedure will be described in details below.

A PCR solution was prepared by adding a reaction composition containing dNTP and the like to the phage 1,000,000 pft and respective primer DNA each in 0.2 μM according to the instruction of the kit and the desired DNA flagment was amplified in PCR conditions: keeping at 94° C. for 2 minutes, and further repeating 40 cycles each of which comprised keeping at 94° C. for 30 seconds, at 55° C. for 30 seconds, and at 68° C. for 5 minute. Next, using the amplified DNA flagment as a template, a probe labelled with $^{32}P$ was prepared employing Megaprime DNA-labelling system kit (Amersham Pharmacia Co.). Incidentally, reaction solution (25 μl) was prepared by adding 2.0 MBq of $^{32}P$ dCTP to 25 ng of amplified DNA flagment and adding a reaction composition instructed by the kit. The labelling reaction was carried out at 37° C. for 10 minutes.

Example 3

Production of Phage cDNA Clone Holding CRE1

The cloning of desired CRE1 gene was carried out by plaque hybridization using the probe prepared by the example 1. Detailed description will be given below.

Using the phage cDNA library produced in the example 1 and according to the instruction of ZAP-cDNAR Synthesis Kit, plaque was produced. DNA was adsorbed on a nitrocellulose filter from the produced plaque and then treated with UV rays to be fixed on the filter. Using the filter prepared in such a manner, hybridized phage cDNA clone was obtained by keeping at 65° C. in the presence of 6×SSC (0.9 M NaCl and 0.09 M trisodium citrate), 5×Denhard's solution [0.1% (w/v) ficoll 400, 0.1% (w/v) polyvinylpyrrolidone, 0.1% BSA], 0.5% (w/v) SDS and 100 μg/ml degenerated salmon sperm DNA or in DIG EASY Hyb solution (Boeringer-Mannheim Co.) containing 100 μg/ml of degenerated salmon sperm DNA, successively keeping at a room temperature for 15 minutes two times in the presence of 1×SSC (0.15 M NaCl and 0.015 M trisodium citrate) and 0.5% (w/v) SDS, and further keeping at 68° C. for 30 minutes in the presence of 0.1×SSC (0.015 M NaCl and 0.0015 M trisodium citrate) and 0.5% SDS.

Example 4

Cloning of CRE1 cDNA

Using the cDNA of the phage cDNA clone obtained by the example 3 as a template and DNA having the nucleotide sequence represented by SEQ ID No: 13 and DNA represented by SEQ ID No: 14 as primers, DNA having the nucleotide sequence represented by SEQ ID No: 5 was amplified by PCR. Detailed description will be given below.

The PCR was carried out employing Herculase Enhanced DNA Polymerase (TOYOBO Co., Ltd.) in the reaction conditions of keeping at 94° C. for 1 minute, and further repeating 25 cycles each of which comprised keeping at 94° C. for 30 seconds, at 55° C. for 30 seconds, and at 72° C. for 4 minute. Incidentally, the PCR solution (50 μl) was prepared by adding a reaction composition containing dNTP and the like to 500 ng of cDNA of the phage cDNA clone and respective primer DNA each in 100 ng according to the instruction of the kit.

The desired DNA flagment was amplified in such a manner.

Example 5

Construction of CRE1 Expression Vector

After p415CYC1, a yeast expression vector, [Munberg et al. Gene: 156 119-122 (1995), available from ATCC library (No. 873821)] was digested with a restriction enzyme Sma I and then using T4 DNA ligase, DNA having the nucleotide sequence represented by SEQ ID No: 5 and obtained by the example 3 was ligated downstream of the CYC 1 promoter sequence of the expression vector p415CYC1 as to be integrated to express the desired protein in yeast. The constructed DNA was confirmed to be in the right direction and its nucleotide sequence was confirmed to be the nucleotide sequence represented by SEQ ID No: 6 by an automatic DNA sequencer and then the expression plasmid p415CYC-CRE 1 was obtained.

Example 6

Cloning of AHK3 (AAF99730) cDNA

Seeds of *Arabidopsis thaliana* ecotype Wassilewkija were sterilized with 70% of ethyl alcohol for 1 minute and further sterilized with 1.5% of sodium hypochlorite for 10 minutes. The resulting seeds were well washed with sterilized water and then cultured for 2 weeks in GM culture medium [4.3 g Murashige and Skoog's basal salt mixture, 1% sucrose, 10 ml pf 5% MES-KOH (pH 5.7), 0.3 PHYTAGEL™ (gellan gum) (SIGMA)] to obtain 5 g of the plant. After the plant was frozen in liquified nitrogen and physically milled with a mortar and pestle. The resulting milled product was mixed with a mixed solution of 10 ml of an extraction buffer [200 mM Tris-HCl (pH 8.5), 100 mM NaCl, 10 mM EDTA, 0.5% SDS, 14 mM β-mercaptoethanol] and 10 g of phenol. After being mixed with a Voltex mixer, the resulting mixture was mixed further with 10 ml of chloroform and vigorously stirred and subjected to centrifugal separation at 10,000 rotation for 20 minutes. The recovered aqueous layer was mixed with LiCl in the concentration to be 2M of the final concentration, left still at −80° C. for 3 hours, thawed and subjected to centrifugal separation at 10,000 rotation for 20 minutes to recover a precipitate. The recovered precipitate was dissolved in 2 ml of TE [10 mM Tris-HCl (pH 8.0), 1 mM EDTA] and then further with 0.2 ml of 3 M sodium acetate (pH 5.2) and 5 ml ethanol and subjected to centrifugal separation to recover RNA as a precipitate. Further, 40 μg of the precipitate (RNA) was mixed with 30 unit of FPLC pure™ DnaseI (RNase free-DNase I) (Amersham-Pharmacia) and 60 unit of Superace (Ambion) to remove mixed genome DNA and the resulting RNA was subjected to the phenol/chloroform treatment and ethanol treatment to purify the RNA. Next, using the purified RNA as a template and oligo (dT) 12-18 (Amersham-Pharmacia) as a primer, RT-PCR was carried out. The RT-PCR was carried out employing Superscript II (GIBCO BRL Co.) at 42° C. for 40 minutes. Incidentally the PT-PCR solution was prepared according to the method described in instruction of the Superscript II.

The desired cDNA was amplified in such a manner.

Using the amplified cDNA as a template and DNA having the nucleotide sequence represented by SEQ ID No: 16 and DNA having the nucleotide sequence represented by SEQ ID No: 17 as primers, DNA having the nucleotide sequence represented by SEQ ID No: 3 was amplified by PCR. The PCR was carried out using Herculase Enhanced DNA Polymerase (TOYOBO Co., Ltd.) in the reaction conditions of keeping at 94° C. for 1 minute, and further repeating 41 cycles each of which comprised keeping at 94° C. for 30 seconds, at 55° C. for 30 seconds, and at 72° C. for 4 minute. Incidentally, the PCR solution (50 μl) was prepared by adding a reaction composition containing dNTP and the like to 500 ng of the template DNA and respective primer DNA each in 100 ng according to the instruction of the kit.

The desired DNA flagment was amplified in such a manner.

Example 7

Construction of pHM-1

After p415CYC1 [Munberg et al. Gene: 156 119-122 (1995); available from ATCC library (No. 87382)] was digested with the restriction enzyme Spe I and BamH I, synthesized DNA flagments (linkers) having the nucleotide sequence represented by SEQ ID Nos: 18 and 15 were inserted to the expression vector p415CTC1 using T4 DNA ligases to newly add the restriction enzyme sites Sac II, Apa I, Nhe I to the plasmid p415CYC1 and construct pHM-1.

Example 8

Construction of AHK3 Expression Vector

After the pHM-1 was digested with the restriction enzyme Sal I and Sac II, and then using T4 DNA ligase, DNA having the nucleotide sequence represented by SEQ ID No: 3 was introduced downstream of the CYC1 promoter sequence of the expression vector pHM-1 as to be integrated to express the desired protein in yeast. The constructed DNA was confirmed to be right in the direction and its nucleotide sequence was confirmed to be right in the sequence by an automatic DNA sequencer and thus the expression plasmid p415CYC-AHK3 was obtained.

Example 9

Cloning of AHK2(BAB09274)cDNA

Using the DNA flagments obtained by the example 6 (the cDNA prepared by reverse transcription of the total RNA) as a template and DNA having the nucleotide sequence represented by SEQ ID No: 19 and DNA having the nucleotide sequence represented by SEQ ID No: 20 as primers, DNA having the nucleotide sequence represented by SEQ ID No: 1 was amplified by PCR. The PCR was carried out employing TAKARA Pfu Turbo denature (Takara Shuzo Co., Ltd.) in the reaction conditions of keeping at 94° C. for 1 minute, and further repeating 30 cycles each of which comprised keeping at 94° C. for 30 seconds, at 55° C. for 30 seconds, and at 72° C. for 4 minute. Incidentally, the PCR solution (50 μl) was prepared by adding a reaction composition containing dNTP and the like to 500 ng of the template DNA and respective primer DNA each in 50 ng according to the instruction of the kit.

The desired DNA flagment was amplified in such a manner.

Example 10

Cloning of AHK2(BAB09274)ΔcDNA

Using the DNA flagments obtained by the example 6 (the cDNA prepared by reverse transcription of the total RNA) as a template and DNA having the nucleotide sequence represented by SEQ ID No: 21 and DNA having the nucleotide sequence represented by SEQ ID No: 22 as primers, PCR was carried out to amplify DNA having the nucleotide sequence represented by SEQ ID No: 1 in which ATG was added to the 5' terminal sites of the nucleotide sequence from the nucleotide numbers 586 to 3531. The PCR was carried out employing TAKARA Pfu Turbo denature (Takara Shuzo Co., Ltd.) in the reaction conditions of keeping at 94° C. for 1 minute, and further repeating 30 cycles each of which comprised keeping at 94° C. for 30 seconds, at 55° C. for 30 seconds, and at 72° C. for 4 minute. Incidentally, the PCR solution (50 μl) was prepared by adding a reaction composition containing dNTP and the like to 500 ng of the template DNA and respective primer DNA each in 50 ng according to the instruction of the kit.

The desired DNA flagment was amplified in such a manner.

Example 1

Construction of AHK2 and AHK2 Δ Expression Vector

After pHM-1 was digested with a restriction enzyme Sac II and Nhe I and then using T4 DNA ligase, DNA flagments obtained by the example 9 and the example 10 were respectively ligated downstream of the CYC 1 promoter sequence of the expression vector pHM-1 as to be integrated to express the desired protein in yeast. The introduced DNA was confirmed to be right in the direction and its nucleotide sequence was confirmed to be right in the sequence by an automatic DNA sequencer and thus the expression plasmid p415CYC-AHK 2 and p415CYC-AHK2Δ were obtained.

Example 12

Production of Transformed Cells TM182-CRE1, TM182-AHK2, TM182-AHK2Δ and TM182-AHK3

Transformation of TM182 (Sln1Δ), Sln1 genetically detected strain, [Maeda T et al. Nature: 369 242-245 (1994)] was carried out using the obtained expression plasmid p415CYC-CRE1 (the example 5), p415CYC-AHK2 (the example 11), p415CYC-AHK2Δ (the example 11) and p415CYC-AHK3 (the example 8). The transformation was carried out by employing Polyethylene glycol/lithium acetate (PEG/LiAc)-mediated transformation method according to the description of VII. Library Transformation & Screening Protocols disclosed in MATCHAMAKER Two-Hybrid System 3 User Manual p. 22 from CLONTECH Co. Transformed cells TM182-CRE1, TM182-AHK2, TM182-AHK2Δ and TM182-AHK3 were produced by selecting in the DOLU+Gal culture medium based on disappearance of leucine nutrient requirement in the transformed cell.

Example 13

Response of Transformed Cells TM182-CRE1, TM182-AHK2, TM182-AHK2Δ and TM182-AHK3 to cytokinin (Part 1)

A culture solution 10 μl (about 800 clones of yeast) of the transformed cells TM182-CRE1, TM182-AHK2, TM182-AHK2Δ and TM182-AHK3 produced by the example 12 was spotted on DOLU+Gul agar media containing 10 μM of trans-zeatin and cultured at 30° C. for 30 hours. After incubation, the growth state of the transformed cells was observed and photographed by a digital camera.

As a result, any of the transformed cells TM182-CRE1, TM182-AHK2, TM182-AHK2Δ and TM182-AHK3 showed high growth in the case of using the DOLU+Gul agar culture media containing trans-zeatin as compared with that in the case of using the DOLU+Gul agar culture media containing no trans-zeatin. The results showed that the transformed cells responded to cytokinin and that they were possible to be grown in the DOLU+Gul agar culture media. Further the transformed cells were found possible to be grown in the DOLU+Gal agar culture media independently of the existence trans-zeatin.

Example 14

Response of Transformed Cells TM182-CRE1, TM182-AHK2Δ and TM182-AHK2 to cytokinin (Part 2)

Culture solutions of the transformed cells TM182-CRE1, TM182-AHK2Δ and TM182-AHK2 produced by the example 12 were spotted on DOLU+Gul agar media containing cytokinin in a variety of concentrations (1 nM, 10 nM, 100 nM, 1 μM, 10 μM, 100 μM) and cultured at 30° C. for 30 hours. After incubation, the growth state of the transformed cells was observed and photographed by a digital camera. The lowest supply concentrations of trans-zeatin and cis-zeatin in which the respective transformed cells could be grown were shown in Table 1.

TABLE 1

| cytokinin | TM182-CRE1 | TM182-AHK2 | TM182-AHK2Δ |
|---|---|---|---|
| trans-zeatin | 10 μM | 1 μM | 100 nM |
| cis-zeatin | no growth | 10 μM | 1 μM |

Example 15

Method for Searching Substance Having Agonist-activity to Cytokinin Receptor (Part 1)

The transformed cells TM182-CRE1, TM182-AHK2, TM182-AHK2Δ and TM182-AHK3 produced in the example 12 were inoculated in 200 ml of DOLU+Gal culture media and pre-cultured at 30° C. for 36 hours. The pre-cultured solutions were diluted with DOLU+Gul media as to become 0.100 as the optical density ($OD_{600}$) and further the resultants were diluted with DOLU+Gul media at a dilution rate of 1/200 to obtain diluted pre-cultured solutions.

An assay plate was prepared by filling respective wells of a 96-well plate with 20 μl of solutions which were prepared by diluting DMSO solution (10 mM) of each examinee substance with DOLU+Gul medium at a dilution rate of 1/100, said solutions containing each examinee substance to be 100 μM at the final concentration. Simultaneously, an assay plate only filled with 20 μl of solutions which were prepared by diluting DMSO solution with DOLU+Gul medium, said solutions containing no examinee substance, was prepared as the blank sections.

The diluted pre-cultured solutions were added in 200 μl each into the respective wells of both assay plates and cultured at 30° C. for 24 hours and then the optical density ($OD_{620}$) of each well was measured by a plate reader. The agonist-activity of the examinee substances to the cytokinin receptor was detected by comparing the optical density measured in the testing sections to which the examinee substances were added with the optical density measured in the blank sections. The optical density of the culture solutions of the transformed cells in the testing sections to which the examinee substances were added were shown in Table 2. Compound B showing the higher optical density measured in the testing sections to which the examinee substances were added than that in the blank sections were selected as agonist-active substance to the cytokinin receptor.

TABLE 2

| Examinee substance | TM182-AHK2 | TM182-AHK2Δ | TM182-AHK3 |
|---|---|---|---|
| DMSO | 0.01 | 0 | 0.51 |
| Compound A[*1] | 0.01 | 0 | 0.54 |
| Compound B[*2] | 0.45 | 0.89 | 0.88 |

[*1]Abscisic acid (= negative control)
[*2]6-Benzyl aminopurine (= positive control)

Example 16

Method for Searching Substance Having Antagonist-activity to Cytokinin Receptor (Part 2)

The transformed cells TM182-CRE1, TM182-AHK2, TM182-AHK2Δ and TM182-AHK3 produced in the example 12 are inoculated in 200 ml of DOLU+Gal culture media and cultured at 30° C. for 30 hours to obtain pre-cultured solutions.

An assay plate is prepared by filling respective wells of a 96-well plate with 200 μl of each DOLU+Gul medium mixed with 1 μM of trans-zeatin (cytokinin), and into the assay plate is put each examinee substance to be 1 μM at the final concentration. Simultaneously, an assay plate only filled with 200 μl of the DOLU+Gal medium mixed with 1 μM of trans-zeatin is prepared as the blank sections The pre-cultured solutions are added in 20 μl each into the respective wells of both assay plates and cultured at 30° C. for 30 hours and then the optical density of each well is measured by a plate reader. The antagonist-activity of the examinee substances to the cytokinin receptor is detected by comparing the optical density measured in the testing section to which the examinee substances are added with the optical density measured in the blank sections. The examinee substances showing the lower optical density measured in the testing sections to which the examinee substances are added than that in the blank sections are selected as antagonist-active substance to the cytokinin receptor.

Example 17

Method for Searching Substance Having Agonist-activity to Cytokinin Receptor (Part 3)

The transformed cells TM182-CRE1, TM182-AHK2, TM182-AHK2Δ and TM182-AHK3 produced in the example 12 are inoculated in 200 ml of DOLU+Gal culture media and cultured at 30° C. for 30 hours to obtain pre-cultured solutions.

The pre-cultured transformed cells (TM182-CRE1, TM182-AHK2, TM182-AHK2Δ and TM182-AHK3) are spot-added in 10 μl to the respective DOLU+Gul agar culture media to which agonist-active substances to the cytokinin receptor selected by the example 15 are added while their concentration being changed from 10 nM to 100 μM and then is cultured at 30° C. for 30 hours. After incubation, the intensity of the agonist-activity of the examinee substances to the cytokinin receptor is detected and confirmed based on the lowest concentration at which transformed cells (TM182-CRE1, TM182-AHK2, TM182-AHK2Δ and TM182-AHK3) are observed to grow.

Example 18

Method for Searching Substance Having Antagonist-activity to Cytokinin Receptor (Part 4)

The transformed cells TM182-CRE1, TM182-AHK2, TM182-AHK2Δ and TM182-AHK3 produced in the example 12 are inoculated in 200 ml of DOLU+Gal culture media and cultured at 30° C. for 30 hours to obtain pre-cultured solutions.

The pre-cultured transformed cells (TM182-CRE1, TM182-AHK2, TM182-AHK2Δ and TM182-AHK3) are spot-added in 10 μl to the respective DOLU+Gul agar culture media to which antagonist-active substances to the cytokinin receptor selected by the example 16 are added while their concentration being changed from 10 nM to 100 μM and also 10 μM of trans-zeatin (cytokinin) is added and then is cultured at 30° C. for 30 hours. After incubation, the intensity of the antagonist-activity of the examinee substances to the cytokinin receptor is detected and confirmed based on the lowest concentration at which transformed cells (TM182-CRE1, TM182-AHK2, TM182-AHK2Δ and TM182-AHK3) are not observed to grow.

Hereinafter, the medium compositions to be used in the present invention will be described:

| (a) DOLU + GLU culture medium | |
|---|---|
| Bacto-yeast nitrogen base without amino acids | 6.7 g |
| Glucose | 20 g |
| Drop-out mix (x) | 2.0 g |
| Distilled water | 1000 ml |

| (b) DOLU + GAL culture medium | |
|---|---|
| Bacto-yeast nitrogen base without amino acids | 6.7 g |
| Glucose | 20 g |
| Drop-out mix (x) | 2.0 g |
| Distilled water | 1000 ml |

| | | | |
|---|---|---|---|
| Adenine | 0.5 g | Lysine | 2.0 g |
| Alanine | 2.0 g | Methionine | 2.0 g |
| Arginine | 2.0 g | para-Aminobenzoic acid | 0.2 g |
| Asparagine | 2.0 g | Phenylalanine | 2.0 g |
| Aspartic acid | 2.0 g | Proline | 2.0 g |
| Cysteine | 2.0 g | Serine | 2.0 g |
| Glutamine | 2.0 g | Threonine | 2.0 g |
| Glutamic acid | 2.0 g | Trytophan | 2.0 g |
| Glycine | 2.0 g | Tyrosine | 2.0 g |
| Histidine | 2.0 g | Valine | 2.0 g |
| Inositol | 2.0 g | Isoleucine | 2.0 g |

(c) DOLU+GLU Agar Culture Medium
  A solid culture medium prepared by adding 2% (W/V) of agar into the culture medium (a)

(d) DOLU+GAL Agar Culture Medium
  A solid culture medium prepared by adding 2% (W/V) of agar into the culture medium (c)

"Sequence Table Free Text"
SEQ ID No: 9
  Oligonucleotide primer designed for PCR
SEQ ID No: 10
  Oligonucleotide primer designed for PCR
SEQ ID No: 11
  Oligonucleotide primer designed for PCR
SEQ ID No: 12
  Oligonucleotide primer designed for PCR
SEQ ID No: 13
  Oligonucleotide primer designed for PCR
SEQ ID No: 14
  Oligonucleotide primer designed for PCR
SEQ ID No: 15
  Oligonucleotide primer designed for PCR
SEQ ID No: 16
  Oligonucleotide primer designed for PCR
SEQ ID No: 17
  Oligonucleotide primer designed for PCR
SEQ ID No: 18
  Oligonucleotide primer designed for PCR
SEQ ID No: 19
  Oligonucleotide primer designed for PCR
SEQ ID No: 20
  Oligonucleotide primer designed for PCR
SEQ ID No: 21
  Oligonucleotide primer designed for PCR
SEQ ID No: 22
  Oligonucleotide primer designed for PCR

What is claimed is:

1. A method for determining agonist-activity to a cytokinin receptor, comprising:
    (1) bringing an examinee substance into contact with a cell transformed with DNA comprising a cytokinin receptor gene, wherein the transformed cell expresses said cytokinin receptor from said DNA;
    (2) determining an existence or level of intracellular signal transduction from said cytokinin receptor; and
    (3) comparing the existence or level determined in (2) with a second existence or level of intracellular signal transduction from said cytokinin receptor determined in the absence of said examinee substance;
    wherein said cytokinin receptor is selected from the group consisting of:
    (a) a cytokinin receptor comprising the amino acid sequence of SEQ ID NO:6;
    (b) a cytokinin receptor comprising the amino acid sequence of SEQ ID NO:2;
    (c) a cytokinin receptor comprising the amino acid sequence of SEQ ID NO:4;
    (d) a cytokinin receptor comprising the amino acid sequence of amino acids 196 to 1176 of SEQ ID NO:2;
    (e) a cytokinin receptor comprising the amino acid sequence of amino acids 50 to 1176 of SEQ ID NO:2;
    (f) a cytokinin receptor comprising the amino acid sequence of amino acids 32 to 1036 of SEQ ID NO:4;
    (g) a chimera-type cytokinin receptor comprising extracellular regions, transmembrane regions and histidine kinase regions, all of which are obtained from the same cytokinin receptor selected from the group consisting of CRE1, AHK2 and AHK3, and receiver regions which are obtained from the histidine kinase encoded by the gene selected from the group consisting of Sln1 gene of budding yeast, Chey gene of *Salmonella*, RcsC gene of *E. coli* and Phks gene of fission yeast; and
    (h) a cytokinin receptor comprising an amino acid sequence that has 95% or higher identity to the amino acid sequence of (a), (b), (c), (d), (e), or (f), wherein said cytokinin receptor has cytokinin receptor activity.

2. The method according to claim 1, wherein growth of said transformed cell is controlled by intracellular signal transduction from said cytokinin receptor, and wherein said existence or level and said second existence or level of intracellular signal transduction from said cytokinin receptor are determined by measuring growth of said transformed cell.

3. The method according to claim 1, wherein said transformed cell is generated from a host cell, wherein said host cell is improved so as to have a lower histidine kinase activity lower than before the improvement.

4. The method according to claim 1, wherein said transformed cell is generated from a host cell having a lowered histidine kinase activity, wherein said histidine kinase activity was lowered by a defect in one or more histidine kinase genes.

5. The method according to claim 1, wherein said transformed cell is generated from a host cell having no cytokinin receptor.

6. The method according to claim 1, wherein said transformed cell is yeast.

7. The method according to claim 1, wherein said transformed cell is budding yeast.

8. A method for determining agonist-activity to a cytokinin receptor, comprising:
    (1) bringing an examinee substance into contact with a cell transformed with DNA comprising a cytokinin receptor gene, and wherein the transformed cell expresses said cytokinin receptor from said DNA;
    (2) determining an existence or level of intracellular signal transduction from said cytokinin receptor; and
    (3) comparing the existence or level determined in (2) with a second existence or level of intracellular signal transduction from said cytokinin receptor determined in the absence of said examinee substance but in presence of another substance;
    wherein said cytokinin receptor is selected from the group consisting of:
    (a) a cytokinin receptor comprising the amino acid sequence of SEQ ID NO:6;
    (b) a cytokinin receptor comprising the amino acid sequence of SEQ ID NO:2;
    (c) a cytokinin receptor comprising the amino acid sequence of SEQ ID NO:4;
    (d) a cytokinin receptor comprising the amino acid sequence of amino acids 196 to 1176 of SEQ ID NO:2;
    (e) a cytokinin receptor comprising the amino acid sequence of amino acids 50 to 1176 of SEQ ID NO:2;
    (f) a cytokinin receptor comprising the amino acid sequence of amino acids 32 to 1036 of SEQ ID NO:4;
    (g) a chimera-type cytokinin receptor comprising extracellular regions, transmembrane regions and histidine kinase regions, all of which are obtained from the same cytokinin receptor selected from the group consisting of CRE1, AHK2 and AHK3, and receiver regions which are obtained from the histidine kinase encoded by the gene selected from the group consisting of Sln1 gene of budding yeast, Chey gene of *Salmonella*, RcsC gene of *E. coli* and Phks gene of fission yeast; and
    (h) a cytokinin receptor comprising an amino acid sequence that has 95% or higher identity to the amino acid sequence of (a), (b), (c), (d), (e), or (f), wherein said cytokinin receptor has cytokinin receptor activity.

9. The method according to claim 8, wherein another substance is a substance having no agonist-activity to said cytokinin receptor.

* * * * *